United States Patent
Zu

(10) Patent No.: US 10,821,189 B2
(45) Date of Patent: Nov. 3, 2020

(54) CD38 LIGAND-DRUG CONJUGATES FOR TARGETED CANCER THERAPY

(71) Applicants: Youli Zu, Bellaire, TX (US); THE METHODIST HOSPITAL SYSTEM, Houston, TX (US)

(72) Inventor: Youli Zu, Bellaire, TX (US)

( * ) Notice: Subject to any disclaimer, the term of this patent is extended or adjusted under 35 U.S.C. 154(b) by 0 days.

(21) Appl. No.: 15/565,666

(22) PCT Filed: Apr. 8, 2016

(86) PCT No.: PCT/US2016/026672
§ 371 (c)(1),
(2) Date: Oct. 10, 2017

(87) PCT Pub. No.: WO2016/164743
PCT Pub. Date: Oct. 13, 2016

(65) Prior Publication Data
US 2018/0078649 A1 Mar. 22, 2018

Related U.S. Application Data

(60) Provisional application No. 62/145,781, filed on Apr. 10, 2015.

(51) Int. Cl.
| A61K 48/00 | (2006.01) |
| C07H 21/04 | (2006.01) |
| A61K 47/54 | (2017.01) |
| A61K 31/704 | (2006.01) |
| C12N 15/115 | (2010.01) |
| C12N 15/117 | (2010.01) |

(52) U.S. Cl.
CPC .......... *A61K 47/549* (2017.08); *A61K 31/704* (2013.01); *A61K 48/00* (2013.01); *C07H 21/04* (2013.01); *C12N 15/115* (2013.01); *C12N 15/117* (2013.01); *C12N 2310/16* (2013.01); *C12N 2310/351* (2013.01); *C12N 2310/3511* (2013.01)

(58) Field of Classification Search
CPC .......................... A61K 31/44; A61K 2300/00
See application file for complete search history.

(56) References Cited

U.S. PATENT DOCUMENTS

2012/0004278 A1* 1/2012 Chang et al. ........ C12N 15/113
2012/0128586 A1* 5/2012 Calissano et al. .... C12N 15/111

OTHER PUBLICATIONS

Barbas et al. (Future Oncology, Aptamer applications for targeted cancer therapy, 2010, vol. 6, No. 7, pp. 1117-1126).*
Danova et al. (Anticancer research, In Vivo Biological Effects of Pegfilgrastim after Myelosuppressive Chemotherapy in Breast Cancer, 27, 3399-3402, 2007).*

* cited by examiner

*Primary Examiner* — Amy H Bowman
(74) *Attorney, Agent, or Firm* — Michael D. Eisenberg

(57) ABSTRACT

Disclosed are compositions and methods relating to nucleic acid aptamers that specifically target CD38 protein and also selective binding to CD38-expressing cells. The ligand-drug conjugates specifically target CD38-expressing cancer cells and subsequently internalize into the cell.

10 Claims, 22 Drawing Sheets
Specification includes a Sequence Listing.

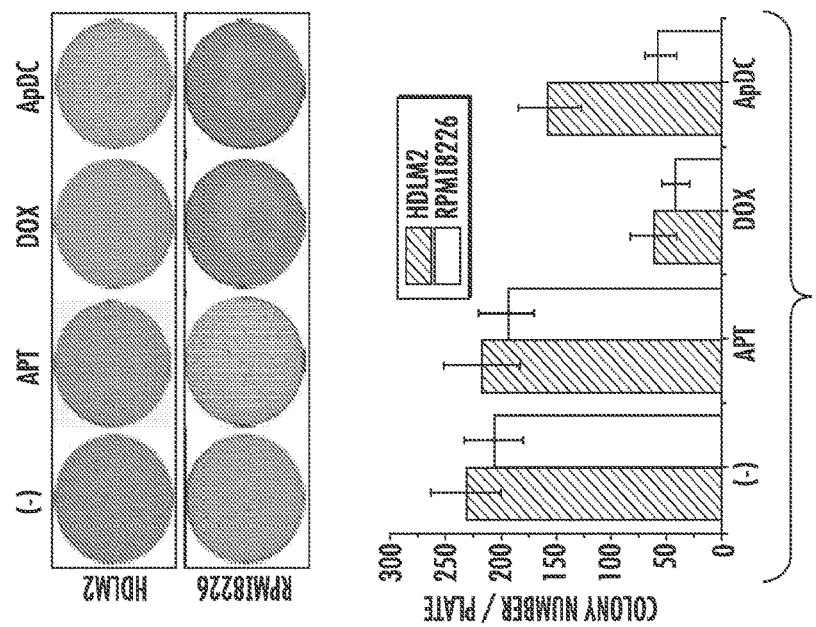
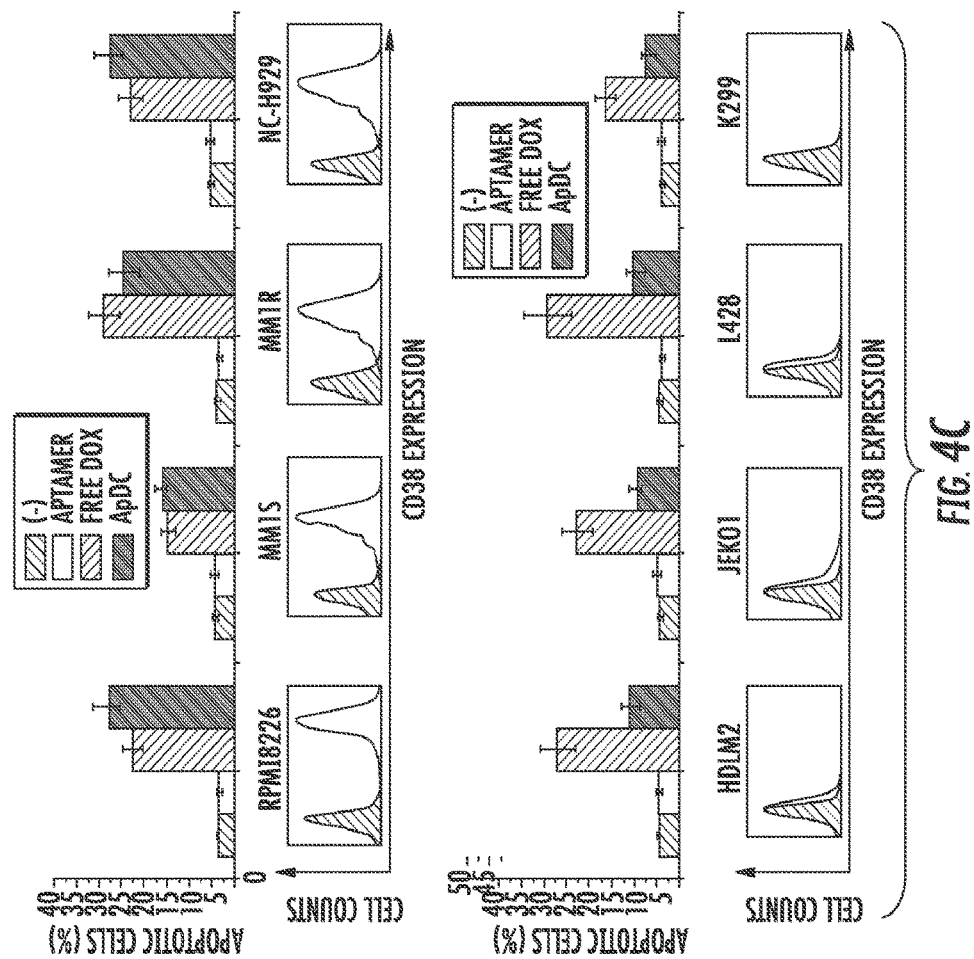
FIG. 4C
FIG. 4D

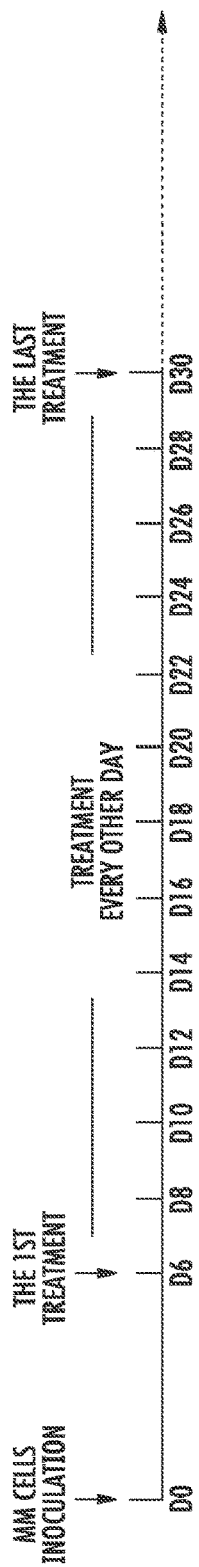
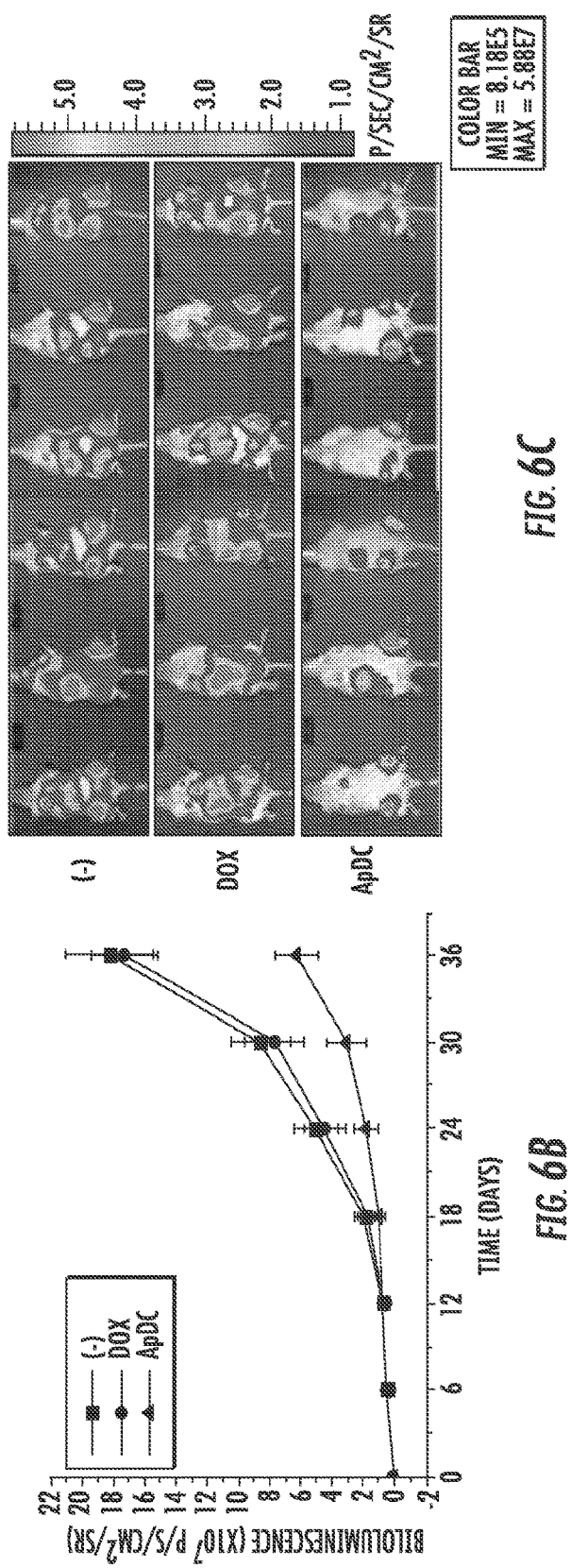
FIG. 6A
FIG. 6B
FIG. 6C

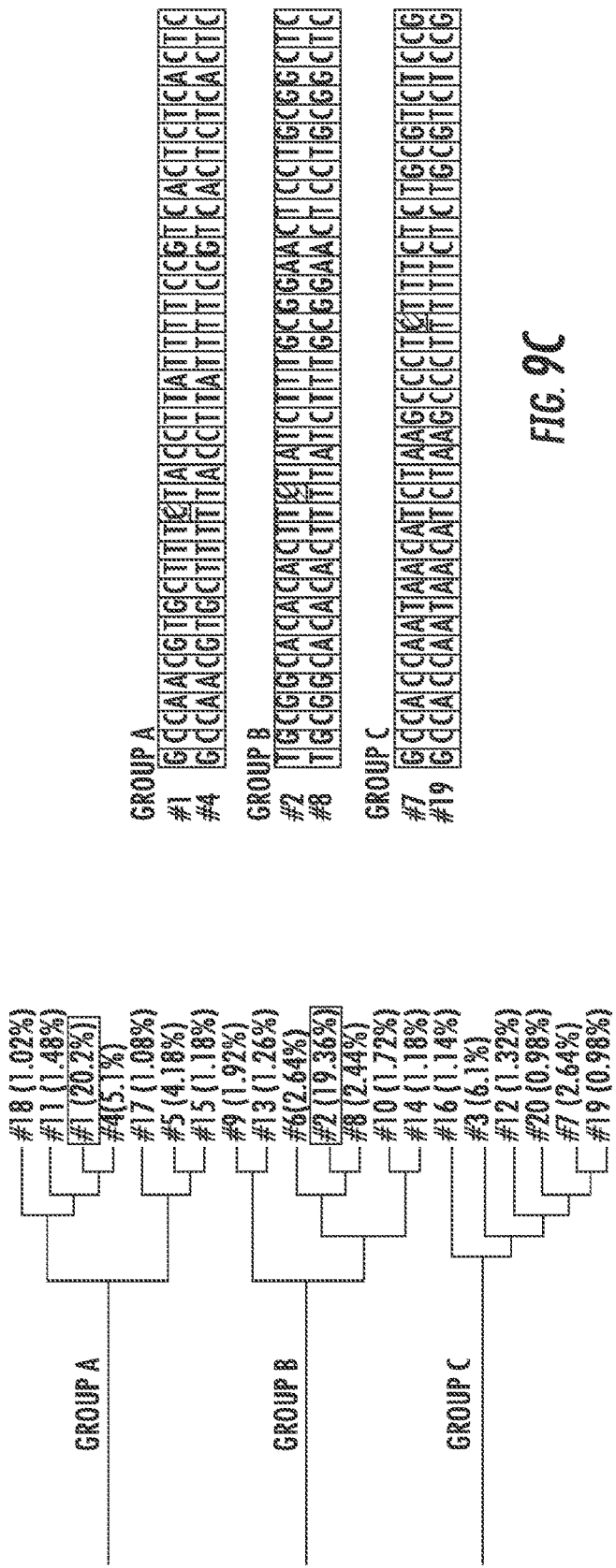

SEQUENCE LISTING

<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (24)..(25)
<223> OTHER INFORMATION: n is a, c, g, or t

<400> SEQUENCE: 1
ggggccgggg caagggggg gtanngtggt aggac         35

<210> SEQ ID NO 2
<211> LENGTH: 61
<212> TYPE: DNA
<213> ORGANISM: Artificial Sequence
<220> FEATURE:
<223> OTHER INFORMATION: Synthetic

<400> SEQUENCE: 2
tccagagtga cgcagcagcc aacgtgcttt ctaccttatt ttccgtcact ctcactctgg         60
a         61

<210> SEQ ID NO 3
<211> LENGTH: 76
<212> TYPE: DNA
<213> ORGANISM: Artificial Sequence
<220> FEATURE:
<223> OTHER INFORMATION: Synthetic
<220> FEATURE:
<221> NAME/KEY: N_region
<222> LOCATION: (19)..(58)
<220> FEATURE:
<221> NAME/KEY: misc_feature
<222> LOCATION: (19)..(58)
<223> OTHER INFORMATION: n is a, c, g, or t

<400> SEQUENCE: 3
atccagagtg acgcagcann nnnnnnnnnn nnnnnnnnnn nnnnnnnnnn nnnnnnnntg         60
gacacggtgg cttagt         76

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
atccagagtg acgcagca                                           18

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
actaagccac cgtgtcca                                           18

<210> SEQ ID NO 6
<211> LENGTH: 41
<212> TYPE: DNA
<213> ORGANISM: Artificial Sequence
<220> FEATURE:
<223> OTHER INFORMATION: Synthetic

<400> SEQUENCE: 6
gccaacgtgc tttttacctt attttccgtc actctctact c                 41

<210> SEQ ID NO 7
<211> LENGTH: 40
<212> TYPE: DNA
<213> ORGANISM: Artificial Sequence
<220> FEATURE:
<223> OTHER INFORMATION: Synthetic

<400> SEQUENCE: 7
tgcggcacac acttctatct ttgcggaact cctgcggctc                   40

<210> SEQ ID NO 8
<211> LENGTH: 40
<212> TYPE: DNA
<213> ORGANISM: Artificial Sequence
<220> FEATURE:
<223> OTHER INFORMATION: Synthetic

<400> SEQUENCE: 8
tgcggcacac acttttatct ttgcggaact cctgcggctc                   40

<210> SEQ ID NO 9
<211> LENGTH: 40
<212> TYPE: DNA
<213> ORGANISM: Artificial Sequence
<220> FEATURE:
<223> OTHER INFORMATION: Synthetic

<400> SEQUENCE: 9
gccaccaata acatctaagc cctctttctc tgcgtctccg                   40

<210> SEQ ID NO 10
<211> LENGTH: 40

```
<212> TYPE: DNA
<213> ORGANISM: Artificial Sequence
<220> FEATURE:
<223> OTHER INFORMATION: Synthetic

<400> SEQUENCE: 10
gccaccaata acatctaagc ccttttctc tgcgtctccg                              40
```

CD38 LIGAND-DRUG CONJUGATES FOR TARGETED CANCER THERAPY

CROSS-REFERENCE TO RELATED APPLICATIONS

This application claims benefit of U.S. Provisional Application No. 62/145,781, filed Apr. 10, 2015, which is hereby incorporated herein by reference in its entirety.

BACKGROUND

Multiple myeloma (MM) is a cancer of plasma cells that originates in the bone marrow (Kyle, R. A., and Rajkumar, S. V. 2004. Multiple myeloma. N Engl J Med 351:1860-1873; Palumbo, A., and Anderson, K. 2011. Multiple myeloma. N Engl J Med 364:1046-1060). In the United States, MM is the second leading hematologic malignancy after non-Hodgkin's lymphoma, with approximately 10,710 myeloma-related deaths recorded in 2013 (Jemal, A., Siegel, R., Xu, J., and Ward, E. 2010. Cancer statistics, 2010. CA Cancer J Clin 60:277-300; Siegel, R., Naishadham, D., and Jemal, A. 2013. Cancer statistics, 2013. CA Cancer J Clin 63:11-30). Despite rapid advances in modern medicine, MM remains incurable (Palumbo, A., and Anderson, K. 2011. Multiple myeloma. N Engl J Med 364:1046-1060), partially due to the lack of targeted therapeutic approaches. New targeted therapeutics are critically needed to treat MM patients.

CD38 is a 46-kDa type II transmembrane glycoprotein and highly expressed by plasma cells (Malavasi, F., Funaro, A., Roggero, S., Horenstein, A., Calosso, L., and Mehta, K. 1994. Human CD38: a glycoprotein in search of a function. Immunol Today 15:95-97). Therapeutic anti-CD38 monoclonal antibodies, including Daratumumab and MOR202, are under clinical investigation (de Weers, M., Tai, Y. T., van der Veer, M. S., Bakker, J. M., Vink, T., Jacobs, D. C., Oomen, L. A., Peipp, M., Valerius, T., Slootstra, J. W., et al. 2011. Daratumumab, a novel therapeutic human CD38 monoclonal antibody, induces killing of multiple myeloma and other hematological tumors. J Immunol 186:1840-1848; Tai, Y. T., and Anderson, K. C. 2011. Antibody-based therapies in multiple myeloma. Bone Marrow Res 2011: 924058). Notably, although CD138 (syndecan-1) is also being used clinically for detection of MM cells in bone marrow specimens, it is not plasma cell-specific, as it is also highly expressed in many non-hematologic tissues, including epithelial cells demonstrated by tissue immunohistochemical stain, and therefore, CD138 is not suitable for targeted MM therapy.

Antibody-drug conjugates (ADC) have emerged by combining a targeting antibody with cytotoxic agents through a linker (Chari, R. V. 2008. Targeted cancer therapy: conferring specificity to cytotoxic drugs. Acc Chem Res 41:98-107; Senter, P. D. 2009. Potent antibody drug conjugates for cancer therapy. Curr Opin Chem Biol 13:235-244; Sievers, E. L., and Senter, P. D. 2013. Antibody-drug conjugates in cancer therapy. Annu Rev Med 64:15-29). The antibody component selectively binds to its cognate biomarker on the surface of tumor cells, followed by receptor-mediated internalization of ADCs and lysosomal trafficking (Ritchie, M., Tchistiakova, L., and Scott, N. 2013. Implications of receptor-mediated endocytosis and intracellular trafficking dynamics in the development of antibody drug conjugates. MAbs 5:13-21), where the drug is released and leads to cancer cell death. By preferentially targeting cancer cells and avoiding healthy tissues, this approach significantly enhances the therapeutic potential of cargo chemotherapeutic agents (Carter, P. J., and Senter, P. D. 2008. Antibody-drug conjugates for cancer therapy. Cancer J 14:154-169; Flygare, J. A., Pillow, T. H., and Aristoff, P. 2013. Antibody-drug conjugates for the treatment of cancer. Chem Biol Drug Des 81:113-121). However, manufacture of ADCs is time- and labor-intensive, and thus, costly.

Aptamers are a new class of small molecule ligands composed of short, single-stranded oligonucleotides about 60-80 bases in length (Parekh, P., Tang, Z., Turner, P. C., Moyer, R. W., and Tan, W. 2010. Aptamers recognizing glycosylated hemagglutinin expressed on the surface of vaccinia virus-infected cells. Anal Chem 82:8642-8649). Aptamers are developed from RNA or ssDNA libraries via a defined experimental process called Systematic Evolution of Ligands by Exponential enrichment (SELEX) (Ellington, A. D., and Szostak, J. W. 1990. In vitro selection of RNA molecules that bind specific ligands. Nature 346:818-822; Tuerk, C., and Gold, L. 1990. Systematic evolution of ligands by exponential enrichment: RNA ligands to bacteriophage T4 DNA polymerase. Science 249:505-510). Similar to protein antibodies, oligonucleotide aptamers specifically recognize and bind to their targets with high affinity on the basis of their unique 3-dimensional structures, and are thus referred to as "chemical antibodies" (Ireson, C. R., and Kelland, L. R. 2006. Discovery and development of anticancer aptamers. Mol Cancer Ther 5:2957-2962).

Aptamer targets include small molecules, macromolecules, viruses, live cells, and tissues (Bruno, J. G., and Kiel, J. L. 1999. In vitro selection of DNA aptamers to anthrax spores with electrochemiluminescence detection. Biosens Bioelectron 14:457-464; Kirby, R., Cho, E. J., Gehrke, B., Bayer, T., Park, Y. S., Neikirk, D. P., McDevitt, J. T., and Ellington, A. D. 2004. Aptamer-based sensor arrays for the detection and quantitation of proteins. Anal Chem 76:4066-4075; Shangguan, D., Li, Y., Tang, Z., Cao, Z. C., Chen, H. W., Mallikaratchy, P., Sefah, K., Yang, C. J., and Tan, W. 2006. Aptamers evolved from live cells as effective molecular probes for cancer study. Proc Natl Acad). Compared to protein antibodies, aptamers offer a number of advantages: they (i) exhibit higher tissue-penetrating potential due to their small size; (ii) appear negligible immunogenicity in vivo; (iii) can be easily conjugated to various functional agents, including chemotherapeutic drugs; and (iv) is able to be simply generated through chemical synthesis at a low cost (Ireson, C. R., and Kelland, L. R. 2006. Discovery and development of anticancer aptamers. Mol Cancer Ther 5:2957-2962; Sundaram, P., Kurniawan, H., Byrne, M. E., and Wower, J. 2013. Therapeutic RNA aptamers in clinical trials. Eur J Pharm Sci 48:259-271; Song, K. M., Lee, S., and Ban, C. 2012. Aptamers and their biological applications. Sensors (Basel) 12:612-63).

What is needed in the art is ssDNA ligands that specifically target CD38 proteins and selectively bind to CD38-expressing cells.

SUMMARY

Disclosed herein are ligand-agent conjugates comprising: a nucleic acid aptamer comprising a region that interacts with a CD38-expressing cell, and an agent. The nucleic acid aptamer can comprise SEQ ID NO: 1 or SEQ ID NO: 2. Also disclosed is a pharmaceutical composition comprising the conjugate, wherein the agent is a therapeutic agent.

Disclosed are methods of targeting CD38-expressing cells with aligandagent conjugate, the method comprising synthesizing a nucleic acid aptamer comprising a region that interacts with a CD38-expressing cell with a CG-Cargo sequence that physically intercalates the agent, and exposing CD38-expressing cells to the ligand-agent conjugate.

Disclosed are methods of inducible intracellular release of the conjugated agent through a structural conformation change of synthesized aptamer/CG-Cargo sequence, which is triggered by low pH microenvironment within particular cellular compartment.

Also disclosed are methods of treating a subject with cancer, the method comprising: identifying a subject in need of treatment for cancer, and administering a pharmaceutical composition to the subject, wherein the pharmaceutical composition comprises a conjugate of a nucleic acid aptamer and a cancer treating agent, wherein the nucleic acid aptamer comprises a region that interacts with a CD38-expressing cell, thereby treating cancer in the subject.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
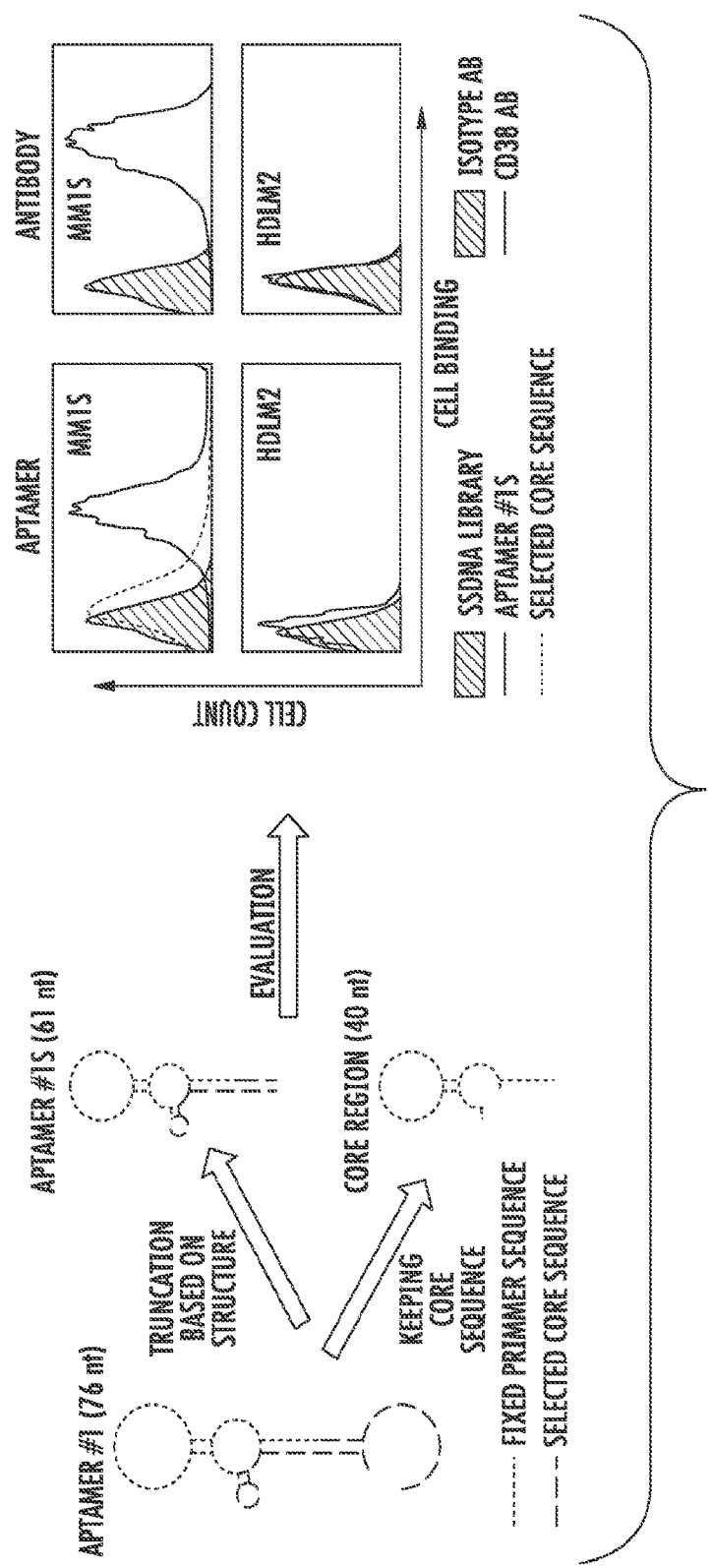
FIG. 1 shows various aptamer affinity and specificity data. Aptamer#1S (SEQ ID NO: 2) shows high affinity and specificity in CD38-expressing MM cells. (A) The sequence of aptamer#1 was truncated based on two different strategies; the binding affinity and specificity of Aptamer#1S was determined in MM and HDLM2 cell lines. (B) Binding affinity and specificity of Aptamer#1S was further compared in CD38+ (RPMI8226 and NCI-H929), and CD38− (K299 and Jeko1) cell lines. (C) MM1S (CD38+) and HDLM2 (CD38-) cells lysates were precipitated with Biotin-conjugated Aptamer#1 and Aptamer#1S, and then probed with anti-CD38 antibody. (D) Binding affinity and specificity of Aptamer#1S was confirmed by fluorescence microscopy in mixture of MM1S and HDLM2 cells.
Figure 1C:
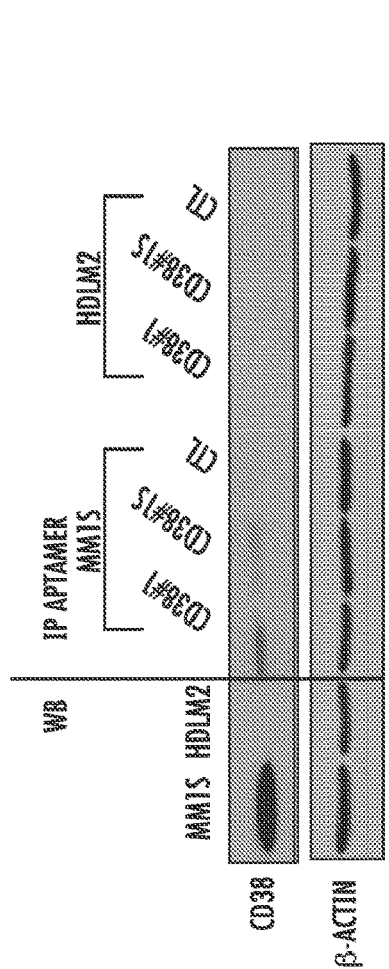

The materials, compounds, compositions, articles, and methods described herein may be understood more readily by reference to the following detailed description of specific aspects of the disclosed subject matter and the Examples included therein and to the Figures.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and, unless a particular term is specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an aptamer" includes mixtures of two or more such aptamers, reference to "the conjugate" includes mixtures of two or more such conjugates, and the like.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides.

Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "olilgonucleotide" or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein.

Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

The term "gene" is used broadly to refer to any segment of nucleic acid associated with a biological function. Genes include coding sequences and/or the regulatory sequences required for their expression. For example, gene refers to a nucleic acid fragment that expresses mRNA, functional RNA, or a specific protein, including its regulatory sequences. Genes also include non-expressed DNA segments that, for example, form recognition sequences for other proteins.

Genes can be obtained from a variety of sources, including cloning from a source of interest or synthesizing from known or predicted sequence information, and may include sequences designed to have desired parameters. In addition, a "gene" or a "recombinant gene" refers to a nucleic acid molecule comprising an open reading frame and including at least one exon and (optionally) an intron sequence. The term "intron" refers to a DNA sequence present in a given gene which is not translated into protein and is generally found between exons.

"Naturally occurring," "native" or "wild type" is used to describe an object that can be found in nature as distinct from being artificially produced. For example, a nucleotide sequence present in an organism (including a virus), which can be isolated from a source in nature and which has not been intentionally modified in the laboratory, is naturally occurring. Furthermore, "wild-type" refers to the normal gene, or organism found in nature without any known mutation.

"Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to nucleic acid aptamers, the nucleic acid molecules of the invention can include other sequences which have a utility in the methods disclosed herein.

As used herein, the term "recombinant nucleic acid," e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"Recombinant DNA molecule" is a combination of DNA sequences that are joined together using recombinant DNA technology and procedures used to join together DNA sequences as described, for example, in Sambrook and Russell (2001).

The terms "heterologous gene," "heterologous DNA sequence," "exogenous DNA sequence," "heterologous RNA sequence," "exogenous RNA sequence" or "heterologous nucleic acid" each refer to a sequence that either originates from a source foreign to the particular host cell, or is from the same source but is modified from its original or native form. Thus, a heterologous gene in a host cell includes a gene that is endogenous to the particular host cell but has been modified through, for example, the use of DNA shuffling. The terms also include non-naturally occurring multiple copies of a naturally occurring DNA or RNA sequence. Thus, the terms refer to a DNA or RNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA or RNA sequence is a sequence that is naturally associated with a host cell into which it is introduced.

"Genome" refers to the complete genetic material of an organism.

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

"Coding sequence" refers to a DNA or RNA sequence that codes for a specific amino acid sequence. It may constitute an "uninterrupted coding sequence", i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The terms "initiation codon" and "termination codon" refer to a unit of three adjacent nucleotides (a 'codon') in a coding sequence that specifies initiation and chain termination, respectively, of protein synthesis (mRNA translation).

"Functional RNA" refers to sense RNA, antisense RNA, ribozyme RNA, siRNA, or other RNA that may not be translated but yet has an effect on at least one cellular process.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

As used herein, the term "derived" or "directed to" with respect to a nucleotide molecule means that the molecule has complementary sequence identity to a particular molecule of interest.

"Treating" as used herein refers to ameliorating at least one symptom of, curing and/or preventing the development of a disease or a condition.

The term "drug", as used herein, refers to a compound that is desirable to use in the body of an animal subject for a therapeutic and/or diagnostic purpose. Accordingly, the term "drug" encompasses, but is not limited to (i) conventional pharmaceutical compounds useful for the treatment of diseases or disorders, including, but not limited to, chemotherapeutic agents, antiinflammatory agents, ionotropic agents, antimicrobial agents, etc.; and hormones; (ii) peptide, protein, and peptidomimetic compounds including, but not limited to cytokines, immunoglobulin molecules and fragments thereof, single chain antibodies, and toxins; as well as (iii) imaging agents such as detectable labels including but not limited to radioactive labels; paramagnetic labels, etc.

An individual who is "suffering from" a disease, disorder, and/or condition has been diagnosed with or displays one or more symptoms of the disease, disorder, and/or condition.

An individual who is "susceptible to" a disease, disorder, and/or condition has not been diagnosed with and/or may not exhibit symptoms of the disease, disorder, and/or condition. In some embodiments, an individual who is susceptible to a disease, disorder, and/or condition (e.g., cancer) may be characterized by one or more of the following: (1) a genetic mutation associated with development of the disease, disorder, and/or condition (e.g. a mutation in an oncogene-encoding gene); (2) a genetic polymorphism associated with development of the disease, disorder, and/or condition (e.g. a polymorphism in the promoter region of an oncogene-encoding gene); (3) increased and/or decreased expression and/or activity of a protein associated with the disease, disorder, and/or condition; (4) habits and/or lifestyles associated with development of the disease, disorder, and/or condition (e.g. smoking, obesity, unhealthy diet, lack of exercise); (5) a family history of the disease, disorder, and/or condition (e.g. parent with cancer); (6) infection by a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

As used herein, the term "target" or "biomarker" refers to any entity that is capable of specifically binding to a particular nucleic acid aptamer. In some embodiments, targets are specifically associated with one or more particular tissue types. In some embodiments, targets are specifically associated with one or more particular cell types. In some embodiments, targets are specifically associated with one or more particular disease states. In some embodiments, targets are specifically associated with one or more particular developmental stages. For example, a cell-specific aptamer can bind at least 3 fold, at least 4 fold, at least 5 fold, at least 6 fold, at least 7 fold, at least 8 fold, at least 9 fold, at least 10 fold, at least 50 fold, at least 100 fold, or at least 1000 fold greater than a control. In some embodiments, a target can comprise a protein, a carbohydrate, a lipid, and/or a nucleic acid, as described herein.

A substance is considered to be "targeted" for the purposes described herein if it specifically bound to a nucleic acid aptamer. In some embodiments, a nucleic acid aptamer specifically binds to a target under stringent conditions. A conjugate comprising a nucleic acid aptamer is considered to be "targeted" if the nucleic acid aptamer specifically binds to a target, thereby delivering the entire conjugate to a specific organ, tissue, cell, extracellular matrix component, and/or intracellular compartment.

As used herein, the phrase "therapeutic agent" refers to any agent that, when administered to a subject, has a therapeutic and/or diagnostic effect and/or elicits a desired biological and/or pharmacological effect.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels. For example, the conjugates disclosed herein can inhibit the growth or proliferation of cancer cells.

The terms "peptide," "protein," and "polypeptide" are used interchangeably to refer to a natural or synthetic molecule comprising two or more amino acids.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "specifically binds", as used herein, when referring to a peptide or receptor, refers to a binding reaction which is determinative of the presence of the protein or polypeptide or receptor in a heterogeneous population of proteins and other biologics. Thus, under designated conditions, a specified aptamer "specifically binds" to its particular "target" when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Compositions and Methods

Figure 7:
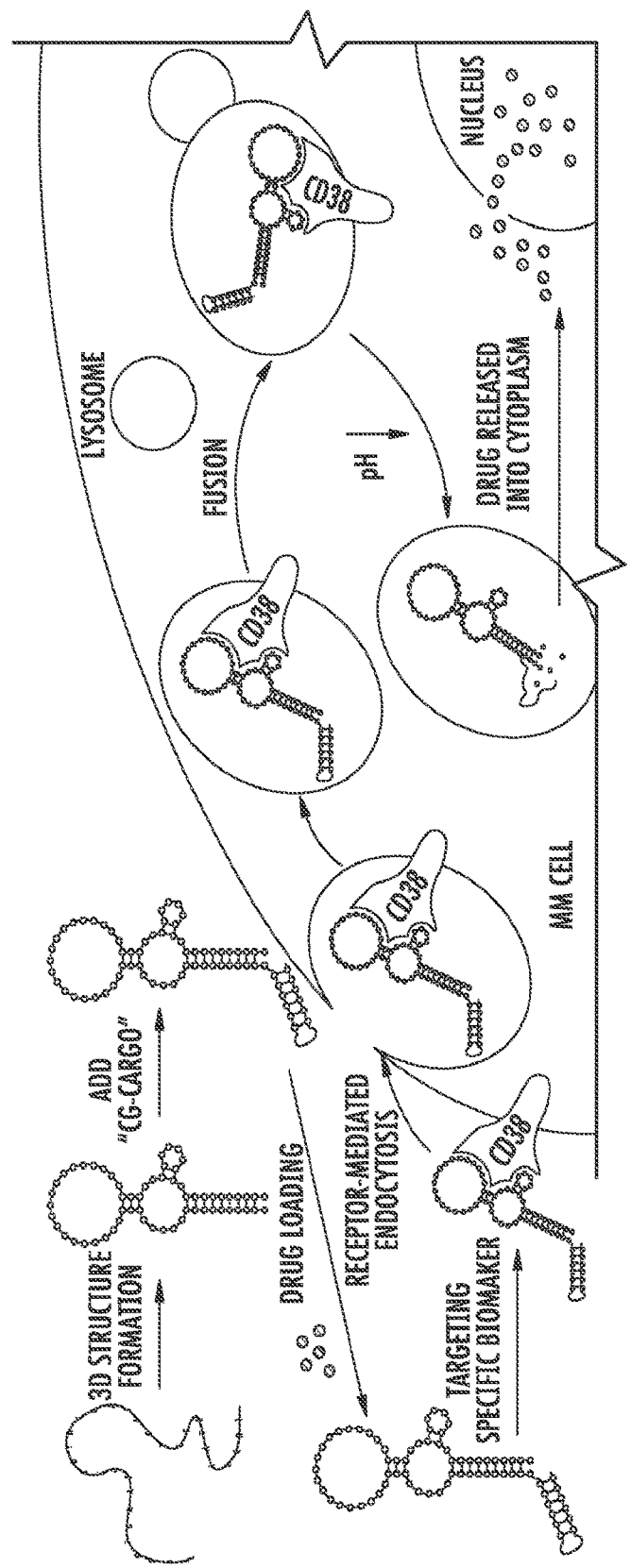
FIG. 7 shows schematic representation of ApDC formation and targeted MM therapy. CD38-specific aptamer were chemically modified to incorporate CG-Cargo structures that allowed high payload of DOX intercalation. Upon specific binding to the cell surface-restricted CD38, ApDC were internalized via receptor-mediated endocytosis. Within cells, endocytic vesicles fused with endosomes and/or lysosomes, and the ApDC secondary structure was disrupted by the decreased pH levels in cellular microenvironment, leading to DOX release to kill MM cells exclusively and have no toxicity to off-target normal cells/tissues.
Figure 8A:
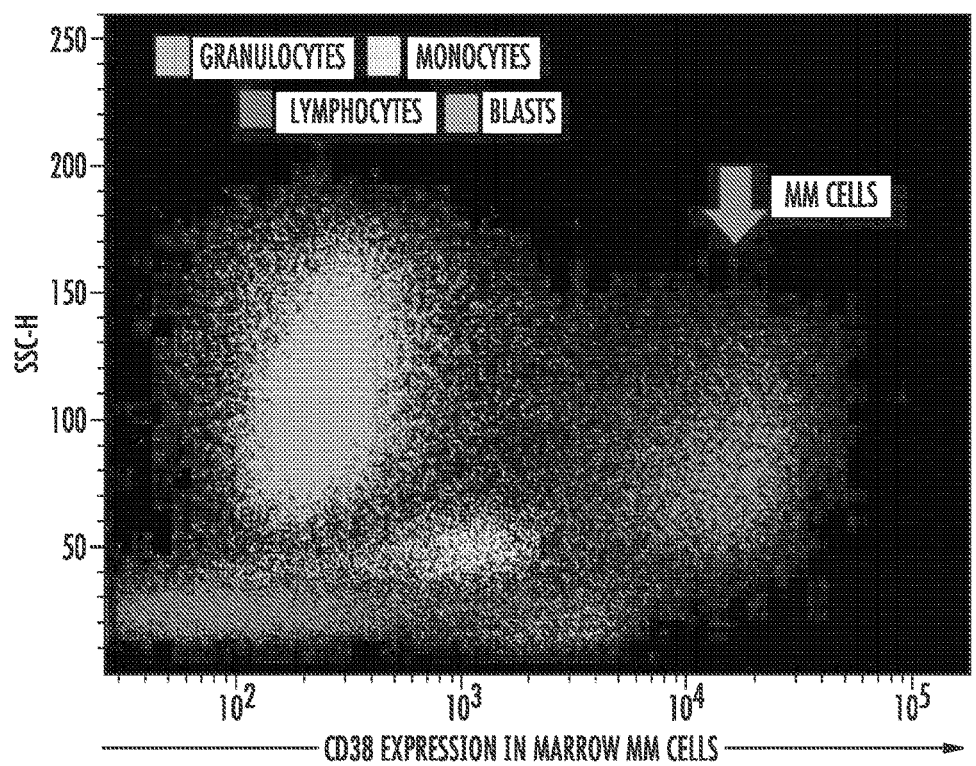
FIG. 8 shows CD38 is a specific biomarker for MM cells. (A) For diagnosis, marrow cells of MM patients were stained with anti-CD38 antibody as well as other relevant antibodies and analyzed by flow cytometry. Different cell populations were gated based on their immunophenotyping profiles and relative levels of CD38 expression were showed. (B) CD138 expression in normal human epithelial cells and plasma cells was determined with immunohistochemical stain.
Figure 8B:
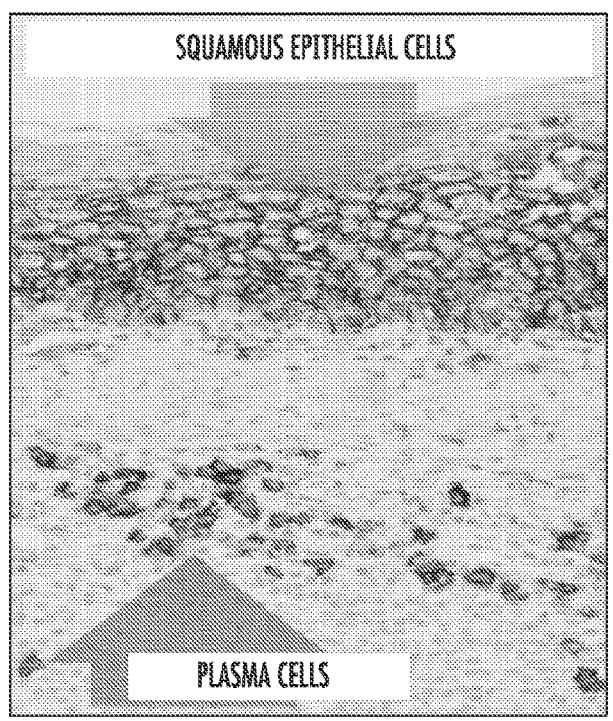

Compared to antibodies, aptamers offer several unique advantages, such as low molecular weight, quick and reproducible synthesis, easy modification, long-term stability, low toxicity, low immunogenicity, and fast tissue penetration (Keefe, A. D., Pai, S., and Ellington, A. 2010. Aptamers as therapeutics. Nat Rev Drug Discov 9:537-550; Germer, K., Leonard, M., and Zhang, X. 2013. RNA aptamers and their therapeutic and diagnostic applications. Int J Biochem Mol Biol 4:27-40). By taking advantage of the aptamer technology and high surface CD38 expression on MM cells, CD38-specific ssDNA aptamers were identified. The ssDNA aptamer was stabile in human serum, able to specifically bind to cultured and patient-derived primary MM cells, and could selectively deliver into MM tumor in vivo. For targeted MM therapy an aptamer-drug conjugate (ApDC, referred to interchangeably herein, or as just "conjugate"), was formulated to carry a high DOX payload (FIGS. 3 and 7). The formed ApDC is stable under normal physiological conditions and can rapidly release drug payload under low pH stimulation (FIG. 3), which is seen within cell lysosome microenvironment. Following a systemic administration, the ApDC aptamer sequence can specifically target CD38 on the surface of MM cells and trigger receptor-mediated internalization. Upon internalization into tumor cells, ApDC is trafficked into lysosomes, where the low pH microenvironment destabilizes the ApDC structural comformation and trigger rapid release of DOX, resulting in MM cell death and inhibition of tumor growth (FIG. 7). Notably, under aptamer guidance the ApDC can selectively deliver and accumulate DOX into MM tumor site to reach therapeutic level although a sub-toxic dose was used for systemic administration. In addition, low pH triggered intracellular release of DOX leads to exclusive toxicity to MM cells and no off-target side effect on normal cells/tissues. Therefore, this ApDC-mediated therapeutic approach is able to specifically treat MM by improving therapeutic potential of DOX and eliminate adverse side effect in patients.

Low pH and enzyme-rich environment within cellular lysosomes cause denaturation and degradation of the aptamer/CG-Cargo sequence structure, resulting in release of the carried DOX, and exclusively killing the targeted cancer cells with no off-target adverse effect on normal cells/tissue.

For cell-targeted drug delivery the receptor-mediated internalization approach has been widely used in antibody-drug conjugates, such as brentuximab to treat CD30-expressing lymphomas (Senter, P. D., and Sievers, E. L. 2012. The discovery and development of brentuximab vedotin for use in relapsed Hodgkin lymphoma and systemic anaplastic large cell lymphoma. Nat Biotechnol 30:631-637). However, production of antibody-drug conjugates is time- and labor-consuming. In contrast, oligonucleotide aptamers can be simply chemical-synthesized and easily conjugated with therapeutic agents. In addition, synthetic aptamers are able to carry bigger drug payloads and have higher tissue penetration capacity due to smaller in size (Hicke, B. J., and Stephens, A. W. 2000. Escort aptamers: a delivery service for diagnosis and therapy. J Clin Invest 106:923-928).

Combining ApDC with other therapeutic agents can achieve a synergistic therapeutic effect. Moreover, in addition to chemotherapeutic drugs, oligonucleotide aptamers can also conjugate and deliver siRNA, phototoxic agents, and gelonin (Zhang, Y., Hong, H., and Cai, W. 2011. Tumor-targeted drug delivery with aptamers. Curr Med Chem 18:4185-4194; Meyer, C., Hahn, U., and Rentmeister, A. 2011. Cell-specific aptamers as emerging therapeutics. J Nucleic Acids 2011:904750; Tan, W., Wang, H., Chen, Y., Zhang, X., Zhu, H., Yang, C., Yang, R., and Liu, C. 2011. Molecular aptamers for drug delivery. Trends Biotechnol 29:634-640), or link with different aptamer (Boltz, A., Piater, B., Toleikis, L., Guenther, R., Kolmar, H., and Hock, B. 2011. Bi-specific aptamers mediating tumor cell lysis. J Biol Chem 286:21896-21905) to enhance therapeutic potential. Interestingly, aptamers might be synthesized with both imaging reporters (Wang, T., and Ray, J. 2012. Aptamer-based molecular imaging. Protein Cell 3:739-754) and therapeutic agents, which is able to detect and treat tumor simultaneously, and monitor therapeutic effect in a real time.

Disclosed herein is a targeted therapeutic approach for specific delivery and intracellular release of an agent payload (such as a drug) in cells, such as MM cells, thereby inhibiting tumor growth and improving survival. Notably, the conjugates disclosed herein can be used as a universal platform to treat different tumors by simply replacing the aptamer sequence that targets different biomarkers.

Aptamers

Disclosed herein is a ligand-agent conjugate comprising: a nucleic acid aptamer comprising a region that interacts with a CD38 cell, and an agent.

Nucleic acid aptamers are characterized by a single-strand and have secondary structure that may possess one or more stems (i.e., base-paired regions) as well as one or more non base-paired regions along the length of the stem. These non-base-paired regions can be in the form of a bulge or loop (e.g., internal loop) along the length of the stem(s) and/or a loop at the end of the one or more stem(s) (e.g., hairpin loop). These nucleic acid aptamers possess specificity in binding to a particular target molecule, and they noncovalently bind their target molecule through an interaction such as an ion-ion force, dipole-dipole force, hydrogen bond, van der Waals force, electrostatic interaction, stacking interaction or any combination of these interactions.

As used herein, "nucleic acid" includes both DNA and RNA, in both D and L enantiomeric forms, as well as derivatives thereof (including, but not limited to, 2'-fluoro-, 2'-amino, 2'O-methyl, 5'iodo-, and 5'-bromo-modified polynucleotides). Nucleic acids containing modified nucleotides (Kubik et al., "Isolation and Characterization of 2'fluoro-, 2'amino-, and 2'fluoro-amino-modified RNA Ligands or Human IFN-gamma that Inhibit Receptor Binding," J. Immunol. 159:259-267 (1997); Pagratis et al., "Potent 2'-amino, and 2'-fluoro-2'-deoxyribonucleotide RNA Inhibitors of Keratinocyte Growth Factor," Nat. Biotechnol. 15:68-73 (1997), each which is hereby incorporated by reference in its entirety) and the L-nucleic acids, enantiomeric to natural D-nucleic acids (Klussmann et al., "Mirror-image RNA that Binds D-adenosine," Nat. Biotechnol. 14:1112-1115 (1996) and Williams et al., "Bioactive and nuclease-resistant L-DNA Ligand of Vasopressin," Proc. Natl. Acad. Sci. USA 94:11285-11290 (1997), each which is hereby incorporated by reference in its entirety), and non-natural bases are used to enhance biostability. In addition, the sugar-phosphate backbone can be replaced with a peptide backbone, forming a peptide nucleic acid (PNA), other natural or non-natural sugars can be used (e.g., 2'-deoxyribose sugars), or phosphothioate or phosphodithioate can be used instead of phosphodiester bonds. The use of locked nucleic acids (LNA) is also contemplated.

The aptamers disclosed herein can comprise various sequences. Specifically, the nucleic acid aptamer can comprise SEQ ID NO: 1. (5'-GCCAACGTGCTTTCTACCTT-ATTTTCCGTCACTCTCACTC-3'). This is known as the "core sequence" of the aptamer, as it comprises the region which interacts with CD38. It is contemplated that the core sequence can comprise variants, such as deletions, additions, and substitutions. Specifically, disclosed are variants of SEQ ID NO: 1 with 80%, 85%, 90%, 95%, 96%, 97%, 98%, and 99% homology to SEQ ID NO: 1, for example. For example, the core sequence vary by 1, 2, 3, 4, 5, 6, 7, 8, 9, or 10 nucleotides and still retain functionality. One of skill in the art will understand how to determine which nucleotides can be added, deleted, or substituted, while still allowing functionality of the aptamer, such as interaction with CD38. Sequence identity and homology is discussed in further detail herein.

In addition to the core sequence (SEQ ID NO: 1), the aptamer can comprise nucleic acid sequences both before and after the core sequence. An example of this can be found in SEQ ID NO: 2 (5'-TCCAGAGTGACGCAGCAGC-CAACGTGCTTTCTACCTTATTTTCCGTCACTCT-CACTCT GGA-3'). Also disclosed are variants of SEQ ID NO: 2, with 80%, 85%, 90%, 95%, 96%, 97%, 98%, and 99% homology to SEQ ID NO: 2, for example. Disclosed are variants of SEQ ID NO: 2 which still allow it to retain functionality as an aptamer of CD38. Sequence identity and homology is discussed in further detail herein.

Also disclosed herein are cell lines, vectors, and expression cassettes comprising the nucleic acid sequences disclosed herein, such as SEQ ID NOS: 1 and 2.

The aptamers disclosed herein can comprise a G-C (guanine-cytosine) region. This region can be comprises of contiguous G-C nucleotides, and can reside at either the 5' or 3' end of the nucleic acid aptamer, or can be internal. Typically, the G-C region resides at the 5' end of the nucleic acid, after the "core sequence", or region that interacts with a cell, such as CD38.

The G-C region can provide the structure to the aptamer that allows for interaction between the aptamer and the agent. The G-C region can, for example, comprise at least 60%, 70%, 80%, 90%, or 100% guanine and cytosine nucleotides. In other words, the G-C region can be substantially comprised of G-C nucleotides, but may not be comprised exclusively of G-C nucleotides. The remaining nucleotides can comprise adenine (A), tyrosine (T), or uracil (U), or other nucleotide derivatives, as disclosed herein.

The G-C region can be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more nucleotides in length. The guanine and cytosine residues can alternate (G-C-G-C, for example), or can be in any other pattern (G-G-C-C) or can be randomly placed.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences.

Generally, the comparison window is at least 20 contiguous nucleotides in length, and optionally can be longer. For example, the core sequence (SEQ ID NO: 1) disclosed herein is 40 nucleotides in length, and can be used in the comparison window. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by visual inspection.

(c) As used herein, "sequence identity" or "identity" in the context of two nucleic acid sequences makes reference to a specified percentage of residues in the two sequences that are the same when aligned for maximum correspondence over a specified comparison window, as measured by sequence comparison algorithms or by visual inspection. When percentage of sequence identity is used in reference to proteins, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

(e)(ii) For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the Tm can be approximated from the equation of Meinkoth and Wahl: Tm 81.5° C. +16.6 (log M)+0.41 (% GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide In general, a signal to noise ratio of 2× (or higher) than that observed for an unrelated probe in the particular hybridization assay indicates detection of a specific hybridization.

Very stringent conditions are selected to be equal to the Tm for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Agents

The agent disclosed herein can be any agent that is capable of linking to the nucleic acid aptamer/CG-Cargo sequence. This link can be covalent or non-covalent. For example, the agent can be non-covalently linked to the aptamer/CG-Cargo sequence, such as being intercalated into the nucleic acid aptamer/CG-Cargo sequence. The intercalating agent can intercalate between the base pairs of the GC-rich area of the nucleic acid aptamer. The agent disclosed herein can optionally link with more than one aptamer. For example, the agent can link with 2, 3, 4, 5, 6, 7, 8, 9, 10, or more aptamers.

The agents disclosed herein can include, for example, therapeutic, diagnostic, and/or prophylactic agents. Exemplary agents to be delivered in accordance with the present invention include, but are not limited to, small molecules, organometallic compounds, nucleic acids (such as siRNA and RNAi), proteins (including multimeric proteins, protein complexes, etc.), peptides, lipids, carbohydrates, hormones, metals, radioactive elements and compounds, gelonins, phototoxic agents, drugs, vaccines, immunological agents, etc., and/or combinations thereof. Specifically, the agent can be a chemotherapeutic agent, such as doxorubicin.

The agent can be a therapeutic agent. The therapeutic agent to be delivered may be a mixture of pharmaceutically active agents. For example, a local anesthetic may be delivered in combination with an anti-cancer agent, such as doxorubicin. To give another example, an antibiotic may be combined with an inhibitor of the enzyme commonly produced by bacteria to inactivate the antibiotic (e.g., penicillin and clavulanic acid). The therapeutic agent can specifically target CD38. For example, specific binding of the nucleic acid to a protein of CD38 can result in delivery of the therapeutic agent to CD38. The therapeutic agent can then cause apoptosis of the CD38 cell.

Examples of therapeutic agents which can be used include, but are not limited to an antagonist of fibroblast-growth factor (FGF), hepatocyte growth factor (HGF), tissue factor (TF), protein C, protein S, platelet-derived growth factor (PDGF), heregulin, macrophage-stimulating protein (MSP) or vascular endothelial growth factor (VEGF), or an antagonist of a receptor for epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP), or vascular endothelial growth factor (VEGF), including HER2 receptor, HER3 receptor, c-MET, and other receptor tyrosine kinases.

The agent to be delivered can be a mixture of anti-cancer agents. The conjugates can be administered in combination with one or more of the anti-cancer agents described herein. For example, the conjugate comprising a therapeutic or diagnostic agent capable of intercalation between the base pairs of the nucleic acid aptamer can be administered in combination with an alkylating agent. To provide another example, conjugates comprising an anti-cancer agent to be delivered are administered in combination with hormonal therapy. The growth of some types of tumors can be inhibited by providing or blocking certain hormones. For example, steroids (e.g. dexamethasone) can inhibit tumor growth or associated edema and may cause regression of lymph node malignancies A. Small Molecule Agents In some embodiments, the agent to be delivered is a small molecule and/or organic compound with pharmaceutical activity. In some embodiments, the agent is a clinically-used drug. In some embodiments, the drug is an anti-cancer agent, antibiotic, antiviral agent, anti-HIV agent, anti-parasite agent, anti-protozoal agent, anesthetic, anticoagulant, inhibitor of an enzyme, steroidal agent, steroidal or non-steroidal antiinflammatory agent, antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anticholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anticholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules), inhibitors of DNA, RNA, or protein synthesis, etc.

The therapeutic agent to be delivered can be an anti-cancer agent (i.e. cytotoxic agents). Most anti-cancer agents can be divided in to the following categories: alkylating agents, antimetabolites, natural products, and hormones and antagonists. An example includes doxorubicin.

Anti-cancer agents typically affect cell division and/or DNA synthesis. However, some chemotherapeutic agents do not directly interfere with DNA. To give but one example, tyrosine kinase inhibitors (imatinib mesylate/GLEEVEC™) directly target a molecular abnormality in certain types of cancer (chronic myelogenous leukemia, gastrointestinal stromal tumors, etc.).

Alkylating agents are so named because of their ability to add alkyl groups to many electronegative groups under conditions present in cells. Alkylating agents typically function by chemically modifying cellular DNA. Exemplary alkylating agents include nitrogen mustards (e.g. mechlorethamine, cyclophosphamide, ifosfamide, melphalan (1-sarcolysin), chlorambucil), ethylenimines and methylmelamines (e.g. altretamine (hexamethylmelamine; HMM), thiotepa (Methylene thiophosphoramide), triethylenemelamine (TEM)), alkyl sulfonates (e.g. busulfan), nitrosureas (e.g. carmustine (BCNU), lomustine (CCMU), semustine (methyl-CCNU), streptozocin (streptozotocin)), and triazenes (e.g. dacarbazine (DTIC; dimethyltriazenoimidazolecarboxamide)).

Antimetabolites act by mimicking small molecule metabolites (e.g. folic acid, pyrimidines, and purines) in order to be incorporated into newly synthesized cellular DNA. Such agents also affect RNA synthesis. An exemplary folic acid analog is methotrexate (amethopterin). Exemplary pyrimidine analogs include fluorouracil (5-fluorouracil; 5-FU), floxuridine (fluorodeoxyuridine; FUdR), and cytarabine (cytosine arabinoside). Exemplary purine analogs include mercaptopurine (6-mercaptopurine; 6-MP), azathioprine, thioguanine (6-thioguanine; TG), fludarabine phosphate, pentostatin (2'-deoxycoformycin), cladribine (2-chlorodeoxyadenosine; 2-CdA), and erythrohydroxynonyladenine (EHNA).

Natural small molecule products which can be used as anti-cancer agents include plant alkaloids and antibiotics. Plant alkaloids and terpenoids (e.g. vinca alkaloids, podophyllotoxin, taxanes, etc.) typically block cell division by preventing microtubule function. Vinca alkaloids (e.g. vincristine, vinblastine (VLB), vinorelbine, vindesine, etc.) bind to tubulin and inhibit assembly of tubulin into microtubules. Vinca alkaloids are derived from the Madagascar periwinkle, *Catharanthus roseus* (formerly known as *Vinca rosea*). Podophyllotoxin is a plant-derived compound used to produce two other cytostatic therapeutic agents, etoposide and teniposide, which prevent cells from entering the G1 and S phases of the cell cycle. Podophyllotoxin is primarily obtained from the American Mayapple (*Podophyllum peltatum*) and a Himalayan Mayapple (*Podophyllum hexandrum*). Taxanes (e.g. paclitaxel, docetaxel, etc.) are derived from the Yew Tree. Taxanes enhance stability of microtubules, preventing the separation of chromosomes during anaphase.

Antibiotics which can be used as anti-cancer agents include dactinomycin (actinomycin D), daunorubicin (daunomycin; rubidomycin), doxorubicin, idarubicin, bleomycin, plicamycin (mithramycin), and mitomycin (mytomycin C).

Other small molecules which can be used as anti-cancer agents include platinum coordination complexes (e.g. cisplatin (cω-DDP), carboplatin), anthracenedione (e.g. mitoxantrone), substituted urea (e.g. hydroxyurea), methylhydrazine derivatives (e.g. procarbazine (N-methylhydrazine, MIH), and adrenocortical suppressants (e.g. mitotane (o,p'-DDD), aminoglutethimide).

Hormones which can be used as anti-cancer agents include adrenocorticosteroids (e.g. prednisone), aminoglutethimide, progestins (e.g. hydroxyprogesterone caproate, medroxyprogesterone acetate, megestrol acetate), estrogens (e.g. diethylstilbestrol, ethinyl estradiol), antiestrogen (e.g. tamoxifen), androgens (e.g. testosterone propionate, fluoxymesterone), antiandrogens (e.g. flutamide), and gonadotropin-releasing hormone analog (e.g. leuprolide).

Topoisomerase inhibitors act by inhibiting the function of topoisomerases, which are enzymes that maintain the topology of DNA. Inhibition of type I or type II topoisomerases interferes with both transcription and replication of DNA by upsetting proper DNA supercoiling. Some exemplary type I topoisomerase inhibitors include camptothecins (e.g. irinotecan, topotecan, etc.). Some exemplary type II topoisomerase inhibitors include amsacrine, etoposide, etoposide phosphate, teniposide, etc., which are semisynthetic derivatives of epipodophyllotoxins, discussed herein.

B. Nucleic Acid Agents

The conjugates disclosed herein can be used to deliver one or more nucleic acids (e.g. functional nucleic acid bases, functional RNAs, functional DNAs, etc.) to a specific location such as an organ, tissue, cell, extracellular matrix component, and/or intracellular compartment.

In general, a "functional RNA" is an RNA that does not code for a protein but instead belongs to a class of RNA molecules whose members characteristically possess one or more different functions or activities within a cell. It will be appreciated that the relative activities of functional RNA molecules having different sequences may differ and may depend at least in part on the particular cell type in which the RNA is present. Thus the term "functional RNA" is used herein to refer to a class of RNA molecule and is not intended to imply that all members of the class will in fact display the activity characteristic of that class under any particular set of conditions. In some embodiments, functional RNAs include RNAi-inducing entities (e.g. short interfering RNAs (siRNAs), short hairpin RNAs (shRNAs), and microRNAs), ribozymes, tRNAs, rRNAs, RNAs useful for triple helix formation, etc.

RNAi is an evolutionarily conserved process in which presence of an at least partly double-stranded RNA molecule in a eukaryotic cell leads to sequence-specific inhibition of gene expression. RNAi was originally described as a phenomenon in which the introduction of long dsRNA (typically hundreds of nucleotides) into a cell results in degradation of mRNA containing a region complementary to one strand of the dsRNA (U.S. Pat. No. 6,506,559; and Fire et al., 1998, Nature, 391:806). Subsequent studies in Drosophila showed that long dsRNAs are processed by an intracellular RNase Ill-like enzyme called Dicer into smaller dsRNAs primarily comprised of two approximately 21 nucleotide (nt) strands that form a 19 base pair duplex with 2 nt 3' overhangs at each end and 5'-phosphate and 3'-hydroxyl groups (see, e.g., PCT Publication WO 01/75164; U.S. Patent Application Publications 2002/0086356 and 2003/0108923; Zamore et al, 2000, Cell, 101:25; and Elbashir of al., 2001, Genes Dev., 15:188).

Short dsRNAs having structures such as this, referred to as siRNAs, silence expression of genes that include a region that is substantially complementary to one of the two strands. This strand is referred to as the "antisense" or "guide" strand, with the other strand often being referred to as the "sense" strand. The siRNA is incorporated into a ribonucleoprotein complex termed the RNA-induced silencing complex (RISC) that contains member(s) of the Argonaute protein family. Following association of the siRNA with RISC, a helicase activity unwinds the duplex, allowing an alternative duplex to form the guide strand and a target mRNA containing a portion substantially complementary to the guide strand. An endonuclease activity associated with the Argonaute protein(s) present in RISC is responsible for "slicing" the target mRNA, which is then further degraded by cellular machinery.

It will be appreciated that molecules having the appropriate structure and degree of complementarity to a target gene will exhibit a range of different silencing efficiencies. A variety of additional design criteria have been developed to assist in the selection of effective siRNA sequences. Numerous software programs that can be used to choose siRNA sequences that are predicted to be particularly effective to silence a target gene of choice are available (see, e.g., Yuan et al., 2004, Nucl. Acids. Res., 32:W130; and Santoyo et al, 2005, Bioinformatics, 21:1376).

As will be appreciated by one of ordinary skill in the art, RNAi may be effectively mediated by RNA molecules having a variety of structures that differ in one or more respects from that described above. For example, the length of the duplex can be varied (e.g., from about 17-29 nucleotides); the overhangs need not be present and, if present, their length and the identity of the nucleotides in the overhangs can vary (though most commonly symmetric dTdT overhangs are employed in synthetic siRNAs).

Additional structures, referred to as short hairpin RNAs (shRNAs), are capable of mediating RNA interference. An shRNA is a single RNA strand that contains two complementary regions that hybridize to one another to form a double-stranded "stem," with the two complementary regions being connected by a single-stranded loop. shRNAs are processed intracellularly by Dicer to form an siRNA structure containing a guide strand and an antisense strand. While shRNAs can be delivered exogenously to cells, more typically intracellular synthesis of shRNA is achieved by introducing a plasmid or vector containing a promoter operably linked to a template for transcription of the shRNA into the cell, e.g., to create a stable cell line or transgenic organism.

While sequence-specific cleavage of target mRNA is currently the most widely used means of achieving gene silencing by exogenous delivery of short RNAi entities to cells, additional mechanisms of sequence-specific silencing mediated by short RNA entities are known. For example, post-transcriptional gene silencing mediated by small RNA entities can occur by mechanisms involving translational repression. Certain endogenously expressed RNA molecules form hairpin structures containing an imperfect duplex portion in which the duplex is interrupted by one or more mismatches and/or bulges. These hairpin structures are processed intracellularly to yield single-stranded RNA species referred to as known as microRNAs (miRNAs), which mediate translational repression of a target transcript to which they hybridize with less than perfect complementarity. siRNA-like molecules designed to mimic the structure of miRNA precursors have been shown to result in translational repression of target genes when administered to mammalian cells.

A short RNAi entity that is delivered according to the methods of the invention and/or is present in a composition of the invention may be designed to silence any eukaryotic gene. The gene can be a mammalian gene, e.g., a human gene. The gene can be a wild type gene, a mutant gene, an allele of a polymorphic gene, etc. The gene can be disease-associated, e.g., a gene whose over-expression, under-expression, or mutation is associated with or contributes to development or progression of a disease. For example, the gene can be oncogene. The gene can encode a receptor or putative receptor for an infectious agent such as a virus (see, e.g., Dykxhhorn et al., 2003, Nat. Rev. Mol. Cell Biol, 4:457 for specific examples).

The nucleic acid agent can also be a ribozyme. A ribozyme is designed to catalytically cleave target mRNA transcripts may be used to prevent translation of a target mRNA and/or expression of a target (see, e.g., PCT publication WO 90/11364; and Sarver et al., 1990, Science 247:1222). Endogenous target gene expression may be reduced by targeting deoxyribonucleotide sequences complementary to the regulatory region of the target gene (i.e., the target gene's promoter and/or enhancers) to form triple helical structures that prevent transcription of the target gene in target muscle cells in the body (see generally, Helene, 1991, Anticancer Drug Des. 6:569; Helene et al, 1992, Ann, N.Y. Acad. Sci. 660:27; and Maher, 1992, Bioassays 14:807).

C. Protein Agents

The agent to be delivered can be a protein or peptide. In certain embodiments, peptides range from about 5 to about 5000, 5 to about 1000, about 5 to about 750, about 5 to about 500, about 5 to about 250, about 5 to about 100, about 5 to about 75, about 5 to about 50, about 5 to about 40, about 5 to about 30, about 5 to about 25, about 5 to about 20, about 5 to about 15, or about 5 to about 10 amino acids in size. Peptides from panels of peptides comprising random sequences and/or sequences which have been varied consistently to provide a maximally diverse panel of peptides may be used.

The terms "protein," "polypeptide," and "peptide" are used interchangeably herein, typically referring to a polypeptide having a length of less than about 500 to about 1000 amino acids. Polypeptides may contain L-amino acids, D-amino acids, or both and may contain any of a variety of amino acid modifications or analogs known in the art. Useful modifications include, e.g., terminal acetylation, amidation, etc. In some embodiments, polypeptides may comprise natural amino acids, unnatural amino acids, synthetic amino acids, and combinations thereof, as described herein.

The agent to be delivered may be a peptide, hormone, erythropoietin, insulin, cytokine, antigen for vaccination, etc. In some embodiments, the agent to be delivered may be an antibody and/or characteristic portion thereof. In some embodiments, antibodies may include, but are not limited to, polyclonal, monoclonal, chimeric (i.e. "humanized"), single chain (recombinant) antibodies. In some embodiments, antibodies may have reduced effector functions and/or bispecific molecules. In some embodiments, antibodies may include Fab fragments and/or fragments produced by a Fab expression library, as described in further detail above.

D. Carbohydrate Agents

The agent to be delivered can be a carbohydrate, such as a carbohydrate that is associated with a protein (e.g. glycoprotein, proteogycan, etc.). A carbohydrate may be natural or synthetic. A carbohydrate may also be a derivatized natural carbohydrate. In certain embodiments, a carbohydrate may be a simple or complex sugar. In certain embodiments, a carbohydrate is a monosaccharide, including but not limited to glucose, fructose, galactose, and ribose. In certain embodiments, a carbohydrate is a disaccharide, including but not limited to lactose, sucrose, maltose, trehalose, and cellobiose. In certain embodiments, a carbohydrate is a polysaccharide, including but not limited to cellulose, microcrystalline cellulose, hydroxypropyl methylcellulose (HPMC), methylcellulose (MC), dextrose, dextran, glycogen, xanthan gum, gellan gum, starch, and pullulan. In certain embodiments, a carbohydrate is a sugar alcohol, including but not limited to mannitol, sorbitol, xylitol, erythritol, malitol, and lactitol.

E. Lipid Agents

The agent to be delivered can be a lipid, such as a lipid that is associated with a protein (e.g. lipoprotein). Exemplary lipids that may be used in accordance with the present invention include, but are not limited to, oils, fatty acids, saturated fatty acid, unsaturated fatty acids, essential fatty acids, cis fatty acids, trans fatty acids, glycerides, monoglycerides, diglycerides, triglycerides, hormones, steroids (e.g., cholesterol, bile acids), vitamins (e.g. vitamin E), phospholipids, sphingolipids, and lipoproteins.

In some embodiments, the lipid may comprise one or more fatty acid groups or salts thereof. In some embodiments, the fatty acid group may comprise digestible, long chain (e.g., $C_8$-$C_{50}$), substituted or unsubstituted hydrocarbons. In some embodiments, the fatty acid group may be a C10-C20 fatty acid or salt thereof. In some embodiments, the fatty acid group may be a $C_{15}$-$C_{20}$ fatty acid or salt thereof. In some embodiments, the fatty acid group may be a $C_{15}$-$C_{25}$ fatty acid or salt thereof. In some embodiments, the fatty acid group may be unsaturated. In some embodiments, the fatty acid group may be monounsaturated. In some embodiments, the fatty acid group may be polyunsaturated. In some embodiments, a double bond of an unsaturated fatty acid group may be in the cis conformation.

In some embodiments, a double bond of an unsaturated fatty acid may be in the trans conformation.

In some embodiments, the fatty acid group may be one or more of butyric, caproic, caprylic, capric, lauric, myristic, palmitic, stearic, arachidic, behenic, or lignoceric acid. In some embodiments, the fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

F. Diagnostic Agents

The agent to be delivered can be a diagnostic agent. In some embodiments, diagnostic agents include gases; commercially available imaging agents used in positron emissions tomography (PET), computer assisted tomography (CAT), single photon emission computerized tomography, x-ray, fluoroscopy, and magnetic resonance imaging (MRI); anti-emetics; and contrast agents. Examples of suitable materials for use as contrast agents in MRI include gadolinium chelates, as well as iron, magnesium, manganese, copper, and chromium. Examples of materials useful for CAT and x-ray imaging include iodine-based materials.

In some embodiments, the conjugate can comprise a diagnostic agent used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3 A (reviewed in Aime et al, 1998, Chemical Society Reviews, 27:19).

The conjugate can comprise radionuclides as therapeutic and/or diagnostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming the conjugate include, but are not limited to, 123I, 125I, 130I, 131I, 133I, 135I, 47Sc, 72As, 72Se, 90Y, 88Y, 97Ru, 100Pd, 101mRh, 119Sb, 128Ba, 197Hg, 211At, 212Bi, 212Pb, 109Pd, 111In, 67Ga, 68Ga, 67Cu, 75Br, 77Br, "mTc, 14C, 13N, 150, 32P, 33P, and 18F.

A diagnostic agent can be a fluorescent, luminescent, or magnetic moiety. For example, a detectable moiety such as a fluorescent or luminescent dye, etc., can be entrapped, embedded, or encapsulated by a particle core and/or coating layer.

Fluorescent and luminescent moieties include a variety of different organic or inorganic small molecules commonly referred to as "dyes," "labels," or "indicators." Examples include fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Application Publication 2004/0067503; Valeur, B., "Molecular Fluorescence: Principles and Applications," John Wiley and Sons, 2002; Handbook of Fluorescent Probes and Research Products, Molecular Probes, 9th edition, 2002; and The Handbook—A Guide to Fluorescent Probes and Labeling Technologies, Invitrogen, 10th edition, available at the Invitrogen web site).

G. Prophylactic Agents

The agent to be delivered can be a prophylactic agent. In some embodiments, prophylactic agents include vaccines. Vaccines may comprise isolated proteins or peptides, inactivated organisms and viruses, dead organisms and virus, genetically altered organisms or viruses, and cell extracts. Prophylactic agents may be combined with interleukins, interferon, cytokines, and adjuvants such as cholera toxin, alum, Freund's adjuvant, etc. Prophylactic agents may include antigens of such bacterial organisms as *Streptococccus pnuemoniae, Haemophilus influenzae, Staphylococcus aureus, Streptococcus pyrogenes, Corynebacterium diphtheriae, Listeria monocytogenes, Bacillus anthracia, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia rickettsi, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

H. Nutraceutical Agents

The therapeutic agent to be delivered can be a nutraceutical agent. In some embodiments, the nutraceutical agent provides basic nutritional value, provides health or medical benefits, and/or is a dietary supplement. In some embodiments, the nutraceutical agent is a vitamin (e.g. vitamins A, B, C, D, E, K, etc.), mineral (e.g. iron, magnesium, potassium, calcium, etc.), or essential amino acid (e.g. lysine, glutamine, leucine, etc.).

Nutraceutical agents can include plant or animal extracts, such as fatty acids and/or omega-3 fatty acids (e.g. DHA or ARA), fruit and vegetable extracts, lutein, phosphatidylserine, lipoid acid, melatonin, glucosamine, chondroitin, aloe vera, guggul, green tea, lycopene, whole foods, food additives, herbs, phytonutrients, antioxidants, flavonoid constituents of fruits, evening primrose oil, flaxseeds, fish and marine animal oils (e.g. cod liver oil), and probiotics.

Exemplary nutraceutical agents and dietary supplements are disclosed, for example, in Roberts et al., (Nutraceuticals: The Complete Encyclopedia of Supplements, Herbs, Vitamins, and Healing Foods, American Nutraceutical Association, 2001). Nutraceutical agents and dietary supplements are also disclosed in Physicians ' Desk Reference for Nutritional Supplements, 1st Ed. (2001) and The Physicians' Desk Reference or Herbal Medicines, 1st Ed. (2001).

Those skilled in the art will recognize that this is an exemplary, not comprehensive, list of therapeutic or diagnostic agents that can be delivered using the conjugates disclosed herein. Any therapeutic or diagnostic agent may be associated with conjugates for targeted delivery as disclosed herein.

Pharmaceutical Compositions

Disclosed herein are pharmaceutical compositions, wherein the composition comprises aptamer-agent conjugates comprising one or more nucleic acid aptamers and a therapeutically effective amount of one or more agents. For example, the aptamer can comprise 2, 3, 4, or 5 or more agents. As described herein, the agent can be capable of intercalating between the base pairs of the nucleic acid aptamer. Disclosed herein are nucleic acid aptamers and agents; and one or more pharmaceutically acceptable excipients. Also disclosed is a method of administering a pharmaceutical composition comprising a conjugate of a nucleic acid aptamer and an agent to a subject in need thereof is provided.

The phrase "active ingredient" generally refers to a conjugate comprising a nucleic acid aptamer and an agent, as described herein.

The formulations of the pharmaceutical compositions described herein may be prepared by any method known or hereafter developed in the art of pharmaceutics. In general, such preparatory methods include the step of bringing the active ingredient into association with one or more excipients and/or one or more other accessory ingredients, and then, if necessary and/or desirable, shaping and/or packaging the product into a desired single- or multi-dose unit.

The pharmaceutical composition can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient(s), and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations can additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof.

The pharmaceutically acceptable excipient can be at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxy ethylene sorbitan [Tween 60], polyoxy ethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and perfuming agents. In certain embodiments for parenteral administration, conjugates can be mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U. S. P. and isotonic sodium chloride solution, etc. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the active ingredient then depends upon its rate of dissolution which, in turn, may depend upon crystal size and crystalline form. In some embodiments, delayed absorption of a parenterally administered active ingredient is accomplished by dissolving or suspending the drug in an oil vehicle.

Compositions for rectal or vaginal administration are typically suppositories which can be prepared by mixing the conjugates with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tabletting lubricants and other tableting aids such a magnesium stearate and micro crystalline cellulose. In the case of capsules, tablets and pills, the dosage forms may comprise buffering agents. Examples of embedding compositions which can be used include polymeric substances and waxes.

Dosage forms for topical and/or transdermal administration of a conjugate may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the excipients and/or additional ingredients described herein.

The pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 μm to about 7 μm or from about 1 μm to about 6 μm. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 µm and at least 95% of the particles by number have a diameter less than 7 µm. Alternatively, at least 95% of the particles by weight have a diameter greater than 1 µm and at least 90% of the particles by number have a diameter less than 6 µm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 µm to about 200 µm.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 µm to 500 µm. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the excipients and/or additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the excipients and/or additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 µm to about 200 µm, and may further comprise one or more of the excipients and/or additional ingredients described herein.

A pharmaceutical composition of the invention may be prepared, packaged, and/or sold in a formulation suitable for ophthalmic administration. Such formulations may, for example, be in the form of eye drops including, for example, a 0.1%/1.0% (w/w) solution and/or suspension of the active ingredient in an aqueous or oily liquid excipient. Such drops may further comprise buffering agents, salts, and/or one or more other of the excipients and/or additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in Remington: The Science and Practice of Pharmacy 21st ed., Lippincott Williams & Wilkins, 2005.

Administration

A therapeutically effective amount of the disclosed conjugates can be delivered to a patient and/or organism prior to, simultaneously with, and/or after diagnosis with a disease, disorder, and/or condition e.g. cancer). In some embodiments, a therapeutic or diagnostic amount of a conjugate is delivered to a patient and/or organism prior to, simultaneously with, and/or after onset of symptoms of a disease, disorder, and/or condition. In some embodiments, the amount of conjugate is sufficient to treat, alleviate, ameliorate, relieve, delay onset of, inhibit progression of, reduce severity of, and/or reduce incidence of one or more symptoms or features of the disease, disorder, and/or condition.

The compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions disclosed herein can be administered by any route. In some embodiments, the pharmaceutical compositions of the present invention are administered by a variety of routes, including oral, intravenous, intramuscular, intraarterial, intramedullary, intrathecal, subcutaneous, intraventricular, transdermal, interdermal, rectal, intravaginal, intraperitoneal, topical (as by powders, ointments, creams, and/or drops), transdermal, mucosal, nasal, buccal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. The conjugates can be administered parenterally, intravenously, or orally, for example.

The disclosed compositions can be administered directly to an affected site. For example, the conjugates can be administered locally near a tumor and/or may be administered directly to a tumor. In some embodiments, local administration refers to administration of conjugates directly to a specific organ. In some embodiments, local administration refers to administration of conjugates directly to a particular organ, tissue, and/or cell. Local administration may be achieved via injection of conjugates directly into a tumor or in the vicinity of a tumor. Local administration may be achieved by topical administration of conjugates at or near the site of a tumor. Local administration may be achieved by implantation of conjugates at or near a site of a tumor by stereotactic surgery. Local administration may be achieved by implantation of conjugates at or near the site of a tumor during surgical removal of the tumor. In some embodiments, local administration refers to administration of the disclosed conjugates to a specific cell or population of cells.

In general the most appropriate route of administration will depend upon a variety of factors including the nature of the agent (e.g., its stability in the environment of the gastrointestinal tract), the condition of the subject (e.g., whether the subject is able to tolerate oral administration), etc. However, the invention encompasses the delivery of the conjugates by any appropriate route taking into consideration likely advances in the sciences of drug delivery.

The disclosed conjugates can be administered at therapeutic agent in amounts ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Combination Therapy

Disclosed herein are "therapeutic cocktails" comprising the conjugates disclosed herein. Conjugates can comprise a single nucleic acid aptamer which can bind to multiple targets, i.e., different cells or different proteins on the same cell. Also disclosed are different nucleic acid aptamers, and all of the different nucleic acid aptamers can bind to the same target, i.e., the same protein on the same cell, or different proteins on the same cell. Also disclosed are nucleic acid aptamers that interact with different targets. These different targets can be associated with the same cell type, such as CD38. Alternatively, different targets can be associated with different cell types.

It will be appreciated that conjugates of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, a conjugate useful for detecting tumors can be administered concurrently with another agent useful for detecting tumors), or they may achieve different effects (one conjugate useful for detecting tumors, and another useful for treating tumors).

The pharmaceutical compositions disclosed herein can be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, a conjugate or nucleic acid aptamer) may be administered concurrently with another therapeutic agent used to treat the same disorder), and/or they may achieve different effects (e.g., control of any adverse effects). Conjugates can be administered with a second therapeutic agent that is approved by the U.S. Food and Drug Administration. Therapeutically active agents utilized in combination can be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

The conjugates disclosed herein can be administered in combination with any therapeutic agent or therapeutic regimen that is useful to treat, alleviate, ameliorate, relieve, delay onset of, inhibit progression of, reduce severity of, and/or reduce incidence of one or more symptoms or features of cancer. For example, the disclosed conjugates can be administered in combination with traditional cancer therapies including, but not limited to, surgery, chemotherapy, radiation therapy, hormonal therapy, immunotherapy, complementary or alternative therapy, and any combination of these therapies.

The disclosed conjugates can be administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g. chemotherapy, radiation therapy, hormonal therapy, immunotherapy, complementary or alternative therapy) can be employed.

The conjugates can be administered in combination with radiation therapy. Radiation therapy (also known as radiotherapy, X-ray therapy, or irradiation) is the use of ionizing radiation to kill cancer cells and shrink tumors. Radiation therapy can be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g. a target organ, tissue, and/or cell) by damaging their genetic material, preventing tumor cells from growing and dividing. In general, radiation therapy attempts to damage as many tumor cells as possible while limiting harm to nearby healthy organs, tissues, and/or cells. Hence, it is often administered in multiple doses, allowing healthy organs, tissues, and/or cells to recover between fractions.

The disclosed conjugates can be administered in combination with immunotherapy. Immunotherapy is the use of immune mechanisms against tumors which can be used in various forms of cancer, such as breast cancer (e.g. trastuzumab/Herceptin®), leukemia (e.g. gemtuzumab ozogamicin/Mylotarg®), and non-Hodgkin's lymphoma (e.g. rituximab/Rituxan®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

Vaccines can also be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes.

The conjugates which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g. morphine, oxycodone, antiemetics, etc.); nausea and vomiting can be treated with 5-HT3 inhibitors (e.g. dolasetron/ANZEMET™, granisetron/KYTRIL™, ondansetron/ZOFRAN™, palonsetron/ALOXI™) and/or substance P inhibitors (e.g. aprepitant/EMEND™); immunosuppression can be treated with a blood transfusion; infection and/or sepsis can be treated with antibiotics (e.g. penicillins, tetracyclines, cephalosporins, sulfonamides, aminoglycosides, etc.); and so forth.

In addition to the conjugates described above that are useful for simultaneously diagnosing and treating cancer, the conjugates can be administered and/or diagnostic methods may be performed in combination with (e.g. in parallel with) any therapeutic or diagnostic agent or regimen that is useful to diagnose one or more symptoms or features of cancer (e.g. detect the presence of and/or locate a tumor). The conjugates can be used in combination with one or more other diagnostic agents. For example, the conjugates can be used to detect tumors, and can be administered in combination with other agents useful in the detection of tumors. For example, conjugates can be administered in combination with traditional tissue biopsy followed by immunohistochemical staining and serological tests. Alternatively or additionally, the conjugates can be administered in combination with a contrasting agent for use in computed tomography (CT) scans and/or MRI.

Methods of Treatment

Disclosed herein are methods of targeting CD38 cells with an agent, the method comprising conjugating a nucleic acid aptamer comprising a region that interacts with a CD38 cell to the agent, and exposing CD38 cells to the aptamer-agent conjugate. The aptamer can comprise a nucleic acid, such as those found in SEQ ID NO: 1 or SEQ ID NO: 2, for example. The conjugates that can be used with this method are described herein.

Also disclosed are methods of treating a subject with cancer, the method comprising: identifying a subject in need of treatment for cancer, and administering a pharmaceutical composition to the subject, wherein the pharmaceutical composition comprises a conjugate of a nucleic acid aptamer and a cancer treating agent, wherein the nucleic acid aptamer comprises a region that interacts with a CD38 cell, thereby treating cancer in the subject. The aptamer can comprise a nucleic acid, such as those found in SEQ ID NO: 1 or SEQ ID NO: 2, for example. The conjugates that can be used with this method are described herein.

The conjugates disclosed herein can be used to treat, alleviate, ameliorate, relieve, delay onset of, inhibit progression of, reduce severity of, and/or reduce incidence of one or more symptoms or features of a disease, disorder, and/or condition. For example, the conjugates can be used to treat cancer. Cancer types include, but are not limited to carcinoma, including that of the bladder, breast, colon, kidney, liver, lung, ovary, pancreas, stomach, cervix, thyroid and skin; including squamous cell carcinoma; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoctanthoma, seminoma, thyroid follicular cancer and teratocarcinoma.

Specifically, the cancer can be associated with CD38 cells. For example, the cancer can be hematopoietic tumors of lymphoid lineage, including leukemia, non-Hodgkin's lymphoma, acute lymphocytic leukemia, acute lymphoblastic leukemia, B-cell lymphoma, T-cell lymphoma, Burkitt's lymphoma, Hodgkin's lymphoma, hairy cell leukemia, multiple myeloma, chronic lymphocytic leukemia; hematopoietic tumors of myeloid lineage, including acute and chronic myeloid leukemias and promyelocytic leukemia.

The treatment of cancer can comprise administering a therapeutically effective amount of the conjugate to a subject in need thereof, in such amounts and for such time as is necessary to achieve the desired result. In certain embodiments of the present invention a "therapeutically effective amount" of the conjugate is that amount effective for treating, alleviating, ameliorating, relieving, delaying onset of, inhibiting progression of, reducing severity of, and/or reducing incidence of one or more symptoms or features of cancer.

When treating cancer, the tumor size can be reduced or eliminated, or other symptoms of cancer can be reduced or eliminated.

A method for administering a conjugate to a subject suffering from cancer is provided. In some embodiments, such methods comprise administering a therapeutically effective amount of a conjugate to a subject in such amounts and for such time as is necessary to achieve the desired result (i.e. treatment of cancer). In certain embodiments of the present invention a "therapeutically effective amount" of a conjugate is that amount effective for treating, alleviating, ameliorating, relieving, delaying onset of, inhibiting progression of, reducing severity of, and/or reducing incidence of one or more symptoms or features of cancer.

Protocols for treatment can involve administering a therapeutically effective amount of a conjugate to a healthy individual (i.e. a subject who does not display any symptoms of cancer and/or who has not been diagnosed with cancer). For example, healthy individuals can be "immunized" with a conjugate prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with the onset of symptoms of cancer. Of course individuals known to have cancer may receive treatment at any time.

Disclosed herein are methods of treating cancer generally comprising targeted delivery of therapeutic agents via a conjugate comprising a nucleic acid aptamer. Such targeted delivery can be useful for delivery of one or more therapeutic agents that are capable of intercalating between the base pairs of a nucleic acid aptamer. Alternatively or additionally, such targeted delivery can be useful for co-delivery of multiple therapeutic agents.

Methods of Diagnosis

Disclosed herein are conjugates that can be used to diagnose a disease, disorder, and/or condition (e.g., autoimmune disorders; inflammatory disorders; infectious diseases; neurological disorders; cardiovascular disorders; proliferative disorders; respiratory disorders; digestive disorders; musculoskeletal disorders; endocrine, metabolic, and nutritional disorders; urological disorders; psychological disorders; skin disorders; blood and lymphatic disorders; etc.). Disclosed conjugates can be used to diagnose cancer. In some embodiments, such methods of diagnosis can involve the use of conjugates to physically detect and/or locate a tumor within the body of a subject.

Specifically, the nucleic acid aptamers disclosed herein can be conjugated to one or more diagnostic agents. A method for the diagnosis of cancer is provided herein. The diagnosis of cancer comprises administering a therapeutically effective amount of a conjugate as described herein to a subject, in such amounts and for such time as is necessary to achieve the desired result. In certain embodiments, a "therapeutically effective amount" of a conjugate is that amount effective for diagnosing cancer.

Disclosed herein are compositions that comprise agents which have intrinsically detectable properties. In one example, disclosed are agents which do not have intrinsically detectable properties but are associated with a substance which is detectable. Such agents are capable of simultaneously diagnosing and treating cancer. In particular, such agents are capable of treating cancer by delivery of the agent that is intercalated between the base pairs of the nucleic acid aptamer, and such conjugates are capable of diagnosing cancer by delivery of a detectable agent to the site of a tumor.

The agent used for detection can comprise a bulk material that is not intrinsically detectable. The agent can comprise one or more fluorescent, luminescent, or magnetic moieties. For example, the agent may comprise fluorescent or luminescent substances or smaller particles of a magnetic material. In some embodiments, an optically detectable moiety such as a fluorescent or luminescent dye, etc., is entrapped, embedded, or encapsulated by a particle core and/or coating layer. Fluorescent and luminescent moieties include a variety of different organic or inorganic small molecules, as described in further detail herein.

Fluorescence or luminescence can be detected using any approach known in the art including, but not limited to, spectrometry, fluorescence microscopy, flow cytometry, etc. Spectrofluorometers and microplate readers are typically used to measure average properties of a sample while fluorescence microscopes resolve fluorescence as a function of spatial coordinates in two or three dimensions for microscopic objects (e.g., less than approximately 0.1 mm diameter). Microscope-based systems are thus suitable for detecting and optionally quantitating particles inside individual cells.

Flow cytometry measures properties such as light scattering and/or fluorescence on individual cells in a flowing stream, allowing subpopulations within a sample to be identified, analyzed, and optionally quantitated (see, e.g., Mattheakis et ah, 2004, Analytical Biochemistry, 327:200). Multiparameter flow cytometers are available. Laser scanning cytometery can be used (Kamentsky, 2001, Methods Cell Biol., 63:51). Laser scanning cytometry can provide equivalent data to a flow cytometer but is typically applied to cells on a solid support such as a slide. It allows light scatter and fluorescence measurements and records the position of each measurement. Cells of interest may be re-located, visualized, stained, analyzed, and/or photographed. Laser scanning cytometers are available, e.g., from CompuCyte (Cambridge, Mass.).

An imaging system comprising an epifluorescence microscope equipped with a laser (e.g., a 488 nm argon laser) for excitation and appropriate emission filter(s) can be used. The filters can allow discrimination between different populations of particles used in the particular assay. For example, in one embodiment, the microscope is equipped with fifteen 10 nm bandpass filters spaced to cover portion of the spectrum between 520 and 660 nm, which would allow the detection of a wide variety of different fluorescent particles. Fluorescence spectra can be obtained from populations of particles using a standard UV/visible spectrometer.

Detection agents can have detectable optical and/or magnetic properties, though agents that may be detected by other approaches can be used. An optically detectable agent is one that can be detected within a living cell using optical means compatible with cell viability. Optical detection is accomplished by detecting the scattering, emission, and/or absorption of light that falls within the optical region of the spectrum, i.e., that portion of the spectrum extending from approximately 180 nm to several microns. Optionally a sample containing cells is exposed to a source of electromagnetic energy. Absorption of electromagnetic energy (e.g., light of a given wavelength) by the particle or a component thereof can be followed by the emission of light at longer wavelengths, and the emitted light is detected. In some embodiments, scattering of light by the particles is detected. For example, light falling within the visible portion of the electromagnetic spectrum, i.e., the portion of the spectrum that is detectable by the human eye (approximately 400 nm to approximately 700 nm) can be detected. In some embodiments of the invention, light that falls within the infrared or ultraviolet region of the spectrum is detected.

An optical property can be a feature of an absorption, emission, or scattering spectrum or a change in a feature of an absorption, emission, or scattering spectrum. An optical property can be a visually detectable feature such as, for example, color, apparent size, or visibility (i.e. simply whether or not the particle is visible under particular conditions). Features of a spectrum include, for example, peak wavelength or frequency (wavelength or frequency at which maximum emission, scattering intensity, extinction, absorption, etc. occurs), peak magnitude (e.g., peak emission value, peak scattering intensity, peak absorbance value, etc.), peak width at half height, or metrics derived from any of the foregoing such as ratio of peak magnitude to peak width. Certain spectra may contain multiple peaks, of which one is typically the major peak and has significantly greater intensity than the others. Each spectral peak has associated features. Typically, for any particular spectrum, spectral features such as peak wavelength or frequency, peak magnitude, peak width at half height, etc., are determined with reference to the major peak. The features of each peak, number of peaks, separation between peaks, etc., can be considered to be features of the spectrum as a whole. The foregoing features can be measured as a function of the direction of polarization of light illuminating the particles; thus polarization dependence can be measured. Features associated with hyper-Rayleigh scattering can be measured. Fluorescence detection can include detection of fluorescence modes and any of the methods described herein.

Intrinsically fluorescent or luminescent particles, particles that comprise fluorescent or luminescent moieties, plasmon resonant particles, and magnetic particles are among the detectable agents that can be used with the methods disclosed herein. Such agents can have a variety of different shapes including spheres, oblate spheroids, cylinders, shells, cubes, pyramids, rods (e.g., cylinders or elongated structures having a square or rectangular cross-section), tetrapods (particles having four leg-like appendages), triangles, prisms, etc. In general, the particles should have dimensions small enough to allow their uptake by eukaryotic cells. Typically the particles have a longest straight dimension (e.g., diameter) of 200 nm or less. In some embodiments, the particles have a diameter of 100 nm or less. Smaller particles, e.g., having diameters of 50 nm or less, e.g., 5-30 nm, can be used. The term "particle" encompasses atomic clusters, which have a typical diameter of 1 nm or less and generally contain from several (e.g., 3-4) up to several hundred atoms.

The agents for detection can be quantum dots (QDs). QDs are bright, fluorescent nanocrystals with physical dimensions small enough such that the effect of quantum confinement gives rise to unique optical and electronic properties. Semiconductor QDs are often composed of atoms from groups II-VI or III-V in the periodic table, but other compositions are possible (see, e.g., Zheng et ah, 2004, Phys. Rev. Lett., 93:7, describing gold QDs). By varying their size and composition, the emission wavelength can be tuned (i.e., adjusted in a predictable and controllable manner) from the blue to the near infrared. QDs generally have a broad absorption spectrum and a narrow emission spectrum. Thus different QDs having distinguishable optical properties (e.g., peak emission wavelength) can be excited using a single source. QDs are brighter than most conventional fluorescent dyes by approximately 10-fold (Wu et al, 2003, Nat. Biotechnol., 21:41; and Gao et al, 2004, Nat. Biotechnol, 22:969) and have been significantly easier to detect than GFP among background autofluorescence in vivo (Gao et al, 2004, Nat. Biotechnol, 22:969). Furthermore, QDs are less susceptible to photobleaching, fluorescing more than 20 times longer than conventional fluorescent dyes under continuous mercury lamp exposure (Derfus et al, 2004, Advanced Materials, 16:961).

Optically detectable agents can be metal particles. Metals of use include, but are not limited to, gold, silver, iron, cobalt, zinc, cadmium, nickel, gadolinium, chromium, copper, manganese, palladium, tin, and alloys thereof. Oxides of any of these metals can be used. Noble metals (e.g., gold, silver, copper, platinum, palladium) are preferred for plasmon resonant particles, which are discussed in further detail below. For example, gold, silver, or an alloy comprising gold, silver, and optionally one or more other metals can be used. Core/shell particles (e.g., having a silver core with an outer shell of gold, or vice versa) can be used. Particles containing a metal core and a nonmetallic inorganic or organic outer shell, or vice versa, can be used. The nonmetallic core or shell can comprise a dielectric material such as silica. Composite agents in which a plurality of metal particles are embedded or trapped in a nonmetal (e.g., a polymer or a silica shell) may be used. Hollow metal particles (e.g., hollow nanoshells) having an interior space or cavity are used in some embodiments. In some embodiments, a nanoshell comprising two or more concentric hollow spheres is used. Such a particle optionally comprises a core, e.g., made of a dielectric material.

Magnetic particles, or agents, can also be used with the conjugates as disclosed herein for detection. "Magnetic particles" refers to magnetically responsive particles that contain one or more metals or oxides or hydroxides thereof. Such particles typically react to magnetic force resulting from a magnetic field. The field can attract or repel the particle towards or away from the source of the magnetic field, respectively, optionally causing acceleration or movement in a desired direction in space. A magnetically detectable particle is a magnetic particle that can be detected within a living cell as a consequence of its magnetic properties. Magnetic particles may comprise one or more ferrimagnetic, ferromagnetic, paramagnetic, and/or superparamagnetic materials. Useful particles may be made entirely or in part of one or more materials selected from the group consisting of: iron, cobalt, nickel, niobium, magnetic iron oxides, hydroxides such as maghemite (Y—$Fe_2Os$), magnetite ($FeSO_4$), feroxyhyte (FeO(OH)), double oxides or hydroxides of two- or three-valent iron with two- or three-valent other metal ions such as those from the first row of transition metals such as Co(II), Mn(II), Cu(II), Ni(II), Cr(III), Gd(III), Dy(III), Sm(III), mixtures of the aforementioned oxides or hydroxides, and mixtures of any of the foregoing. Additional materials that may be used in magnetic particles include yttrium, europium, and vanadium.

Methods of Making Conjugates

The conjugates disclosed herein can comprise a nucleic acid aptamer, and an agent, such as a therapeutic or diagnostic agent. The agent can be capable of intercalating between the base pairs of the nucleic acid aptamer. Conjugates are typically formed by incubating the therapeutic or diagnostic agent with the nucleic acid aptamer/CG-Cargo sequence.

Conjugates as disclosed herein can be manufactured using any available method. When associating aptamers with agents, it is desirable to have an agent which can be efficiently linked to a negatively charged nucleic acid aptamer using simple chemistry without adversely affecting the 3-dimensional characteristic and conformation of the nucleic acid aptamer/CG-Cargo sequence, and target binding capacity. It is desirable that the conjugate should be able to avoid uptake by the mononuclear phagocytic system after systemic administration so that it is able to reach specific organs, tissues, and/or cells in the body.

The nucleic acid aptamer can be associated with a second therapeutic or diagnostic agent to be delivered. In some embodiments, therapeutic or diagnostic agents are not covalently associated with the aptamer. To give another example, agents may comprise polymers, and therapeutic or diagnostic agents may be associated with the surface of, encapsulated within, and/or distributed throughout the aptamer. Agents are released by diffusion, degradation of the aptamer, and/or combination thereof. In some embodiments, polymers degrade by bulk erosion. In some embodiments, polymers degrade by surface erosion. In some embodiments, therapeutic or diagnostic agents are covalently associated with an aptamer. For such conjugates, release and delivery of the therapeutic or diagnostic agent to a target site occurs by disrupting the association. For example, if an aptamer is associated with an agent by a cleavable linker, the agent is released and delivered to the target site upon cleavage of the linker.

The conjugates can be physically associated with the nucleic acid aptamer. In some embodiments, physical association may be covalent. For example, the aptamer and agent may be directly associated with one another, e.g., by one or more covalent bonds, or may be associated by means of one or more linkers. In some embodiments, the linker forms one or more covalent or non-covalent bonds with the complex and one or more covalent or non-covalent bonds with the aptamer, thereby attaching them to one another.

Any suitable linker can be used in accordance with the present invention. Linkers may be used to form amide linkages, ester linkages, disulfide linkages, etc. Linkers may contain carbon atoms or heteroatoms (e.g., nitrogen, oxygen, sulfur, etc.). Typically, linkers are 1 to 50 atoms long, 1 to 40 atoms long, 1 to 25 atoms long, 1 to 20 atoms long, 1 to 15 atoms long, 1 to 10 atoms long, or 1 to 10 atoms long. Linkers may be substituted with various substituents including, but not limited to, hydrogen atoms, alkyl, alkenyl, alkynl, amino, alkylamino, dialkylamino, trialkylamino, hydroxyl, alkoxy, halogen, aryl, heterocyclic, aromatic heterocyclic, cyano, amide, carbamoyl, carboxylic acid, ester, thioether, alkylthioether, thiol, and ureido groups. As would be appreciated by one of skill in this art, each of these groups may in turn be substituted.

A linker can an aliphatic or heteroaliphatic linker. For example, the linker can a polyalkyl linker. The linker can be a polyether linker. The linker can be a polyethylene linker, such as PEG. The linker can be a short peptide chain, e.g., between 1 and 10 amino acids in length, e.g., 1, 2, 3, 4, or 5 amino acids in length, a nucleic acid, an alkyl chain, etc.

The linker can be a cleavable linker. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g. esterase cleavable linker), ultrasound-sensitive linkers, x-ray cleavable linkers, etc. In some embodiments, the linker is not a cleavable linker.

Any of a variety of methods can be used to associate a linker with an aptamer and agent. General strategies include passive adsorption (e.g., via electrostatic interactions), multivalent chelation, high affinity non-covalent binding between members of a specific binding pair, covalent bond formation, etc. (Gao et al, 2005, Curr. Op. Biotechnol., 16:63). Click chemistry can be used to associate a linker with an agent (e.g. Diels-Alder reaction, Huigsen 1,3-dipolar cycloaddition, nucleophilic substitution, carbonyl chemistry, epoxidation, dihydroxylation, etc.).

A bifunctional cross-linking reagent can be employed. Such reagents contain two reactive groups, thereby providing a means of covalently associating two target groups. The reactive groups in a chemical cross-linking reagent typically belong to various classes of functional groups such as succinimidyl esters, maleimides, and pyridyldisulfides. Exemplary cross-linking agents include, e.g., carbodiimides, N-hydroxysuccinimidyl-4-azidosalicylic acid (NHS-ASA), dimethyl pimelimidate dihydrochloride (DMP), dimethyl-suberimidate (DMS), 3,3'-dithiobispropionimidate (DTBP), N-Succinimidyl 3-[2-pyridyldithio]-propionamido (SPDP), succimidyl α-methylbutanoate, biotinamidohexanoyl-6-amino-hexanoic acid N-hydroxysuccinimide ester (SMCC), succinimidyl-[(N-maleimidopropionamido)-dodecaethyl-eneglycol] ester (NHS-PEO 12), etc. For example, carbodiimide-mediated amide formation and active ester maleimide-mediated amine and sulfhydryl coupling are widely used approaches.

Common schemes for forming a conjugate involve the coupling of an amine group on one molecule to a thiol group on a second molecule, sometimes by a two- or three-step reaction sequence. A thiol-containing molecule may be reacted with an amine-containing molecule using a heterobifunctional cross-linking reagent, e.g., a reagent containing both a succinimidyl ester and either a maleimide, a pyridyldisulfide, or an iodoacetamide. Amine-carboxylic acid and thiol-carboxylic acid cross-linking, maleimide-sulfhydryl coupling chemistries (e.g., the maleimidobenzoyl-N-hydroxysuccinimide ester (MBS) method), etc., may be used. Polypeptides can conveniently be attached to particles via amine or thiol groups in lysine or cysteine side chains respectively, or by an N-terminal amino group. Nucleic acids such as RNAs can be synthesized with a terminal amino group. A variety of coupling reagents (e.g., succinimidyl 3-(2-pyridyldithio)propionate (SPDP) and sulfosuccinimidyl-4-(N-maleimidomethyl)cyclohexane-1-carboxylate (sulfo-SMCC) may be used to associate the various components of conjugates. Agents can be prepared with functional groups, e.g., amine or carboxyl groups, available at the surface to facilitate association with a biomolecule. Any biomolecule can be attached to another molecule described herein using any of the methods described herein.

Exemplary non-covalent interactions include, but are not limited to, charge interactions, affinity interactions, metal coordination, physical adsorption, host-guest interactions, hydrophobic interactions, FI stacking interactions, hydrogen bonding interactions, van der Waals interactions, magnetic interactions, electrostatic interactions, dipole-dipole interactions, etc.

A nucleic acid aptamer can be associated with an agent via charge interactions. For example, an agent may have a cationic surface or may be reacted with a cationic polymer, such as poly(lysine) or poly(ethylene imine), to provide a cationic surface. The agent surface can then bind via charge interactions with a negatively charged complex. One end of the nucleic acid aptamer is, typically, attached to a negatively charged polymer (e.g., a poly(carboxylic acid)) or an additional oligonucleotide sequence that can interact with the cationic polymer surface without disrupting the binding affinity of the nucleic acid aptamer for its target.

An agent can be associated with a nucleic acid aptamer via hydrogen bonding interactions. For example, an oligonucleotide having a particular sequence may be attached to the surface of the agent, and an essentially complementary sequence may be attached to one or both ends of the complex such that it does not disrupt the binding affinity of the nucleic acid aptamer for its target. The nucleic acid aptamer will then bind to the agent via complementary base pairing with the oligonucleotide attached to the agent. Two oligonucleotides are essentially complimentary if about 80% of the nucleic acid bases on one oligonucleotide form hydrogen bonds via an oligonucleotide base pairing system, such as Watson-Crick base pairing, reverse Watson-Crick base pairing, Hoogsten base pairing, etc., with a base on the second oligonucleotide. Typically, it is desirable for an oligonucleotide sequence attached to the agent to form at least about 6 complementary base pairs with a complementary oligonucleotide attached to the nucleic acid aptamer.

Kits

Disclosed herein are kits comprising a conjugate, wherein the conjugate comprises a nucleic acid aptamer and an agent. For example, the invention provides a kit comprising the conjugate and instructions for use. A kit may comprise multiple different conjugates. A kit may comprise any of a number of additional components or reagents in any combination (e.g. pharmaceutically acceptable excipients). All of the various combinations are not set forth explicitly but each combination is included in the scope of the invention.

A kit may include, for example, (i) a complex comprising a nucleic acid aptamer and one or more therapeutic or diagnostic agents to be delivered which are capable of intercalating between the base pairs of the nucleic acid aptamer; (ii) instructions for administering the conjugate to a subject in need thereof.

Kits typically include instructions for use of conjugates. Instructions may, for example, comprise protocols and/or describe conditions for production of complexes or targeted conjugates, administration of conjugates to a subject in need thereof, design of conjugates, etc. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as Styrofoam, etc., may be enclosed. An identifier, e.g., a bar code, radio frequency identification (ID) tag, etc., may be present in or on the kit or in or one or more of the vessels or containers included in the kit. An identifier can be used, e.g., to uniquely identify the kit for purposes of quality control, inventory control, tracking, movement between workstations, etc.

A number of embodiments of the invention have been described. Nevertheless, it will be understood that various modifications may be made without departing from the spirit and scope of the invention. Accordingly, other embodiments are within the scope of the following claims.

EXAMPLES

Figure 9A:
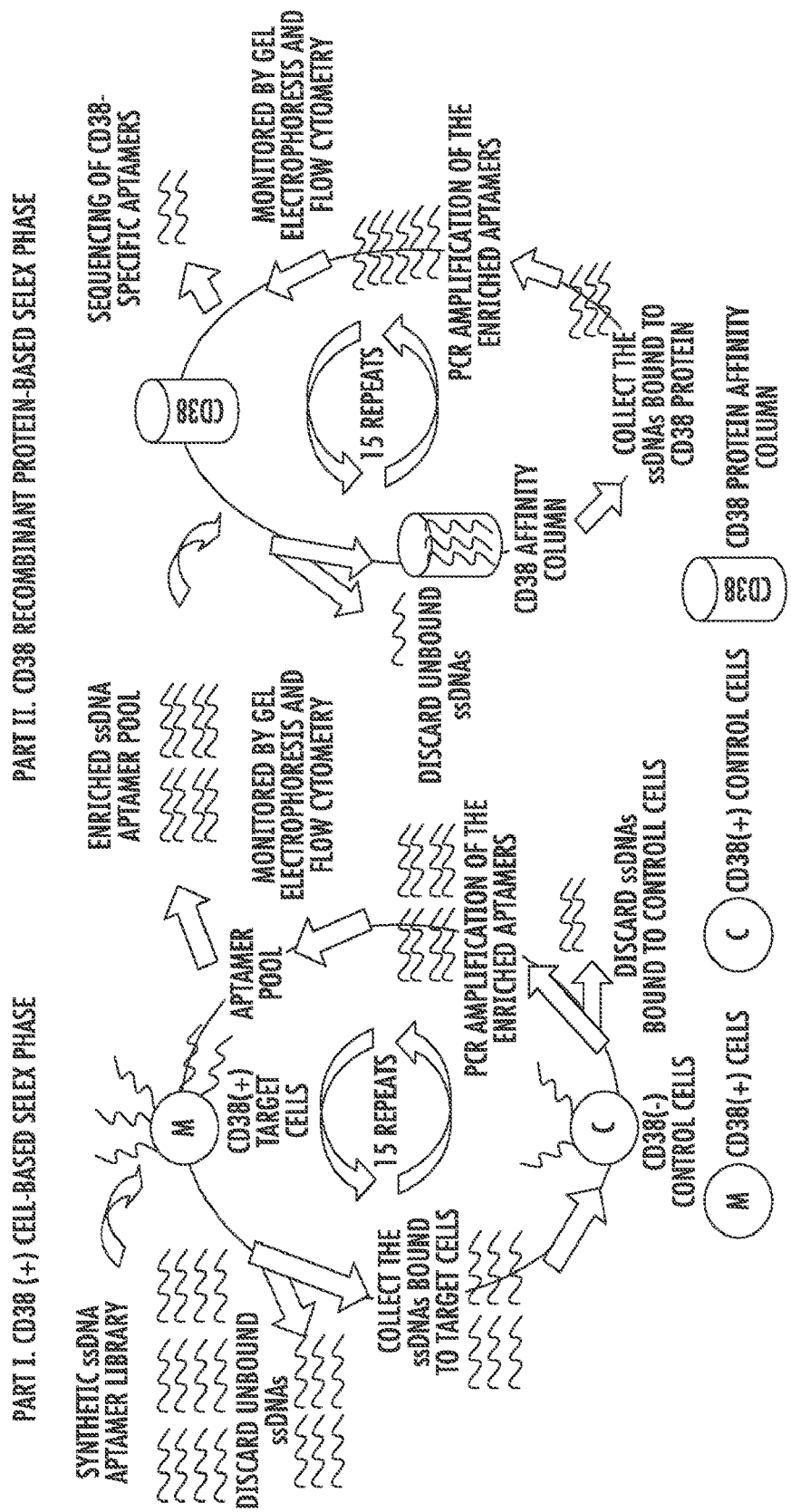
FIG. 9 shows the identification of MM cell-targeted and CD38-specific ssDNA aptamer sequences. (A) Hybrid CD38 aptamer selection includes 15 rounds of MM cell-mediated SELEX (Part I) and 5 rounds of CD38 protein-mediated SELEX (Part II). To obtain sequence information, resultant aptamers were analyzed by next-generation sequencing. (B) Two dominant aptamer sequences, aptamer#1 and apamer#2 were marked in red. In addition, the top 20 aptamer sequences were also subjected to clustal analysis using ClustaX software to generate a phylogenetic tree and clustered into 3 groups that shared a high degree of structural similarity (Groups A, B, and C). (C) Aptamers having single nucleotide-difference are shown, i.e., #1 and #4, #2 and 8#, and #7 and #19 (SEQ ID NOS: 1, 6, 7, 8, 9, and 10, respectively).
Figure 10B:
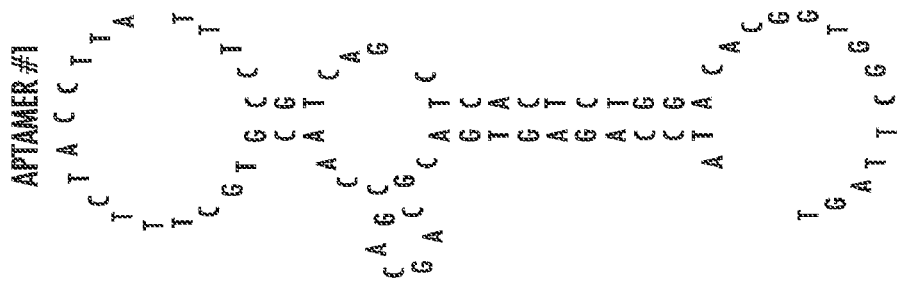
FIG. 10 shows that Aptamer#1 (SEQ ID NO: 2) has high affinity and specificity for CD38+ MM cells. (A) Affinity and specificity of aptamers representing Groups A, B, and C (Aptamer#1, Aptamer#2, and Aptamer#7, respectively) were evaluated in MM1S and HDLM2 cell lines by flow cytometry. Concurrently, CD38 expression in each cell line was determined with anti-CD38 antibody stains. (B) Predicted secondary structure of Aptamer#1 aptamer. (C) Affinity and specificity of Aptamer#1 was further confirmed in various CD38+ (RPMI8226 and NCI-H929) and CD38− (K299 and Jeko1). (D) Affinity Kd of Aptamer#1 and Aptamer#1S in MM1S cells are shown.
Figure 10A:
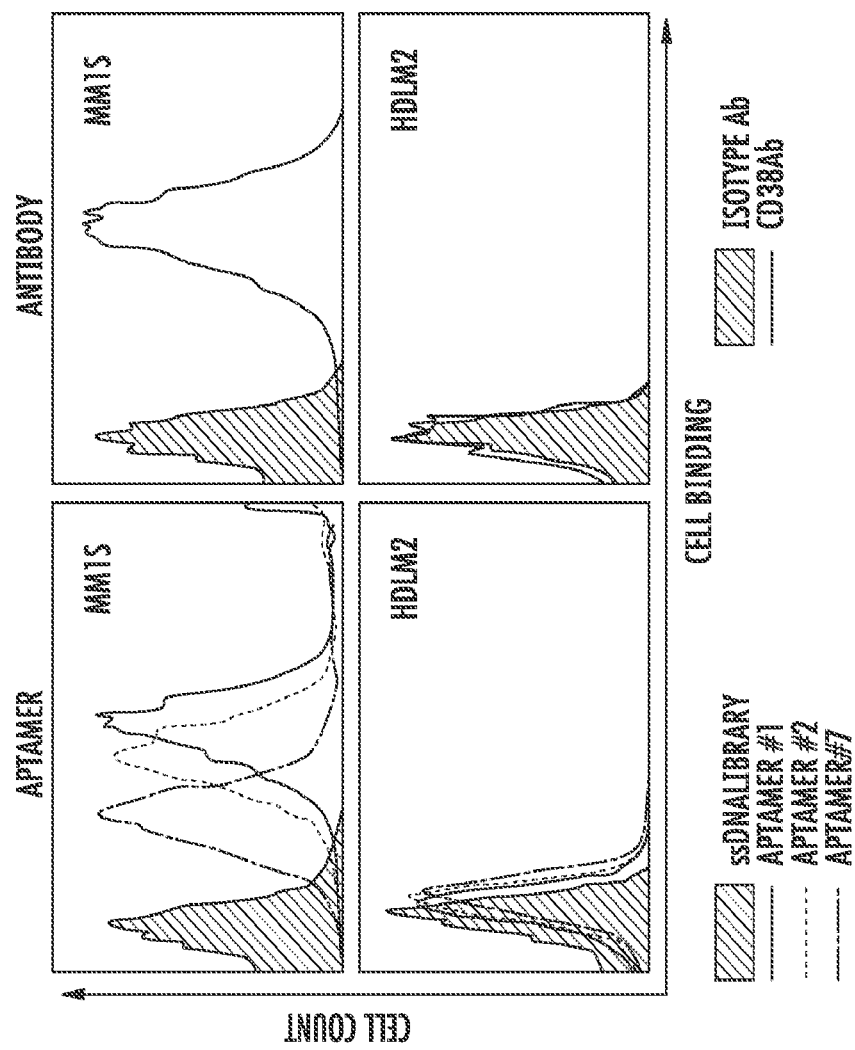
Figure 10C:
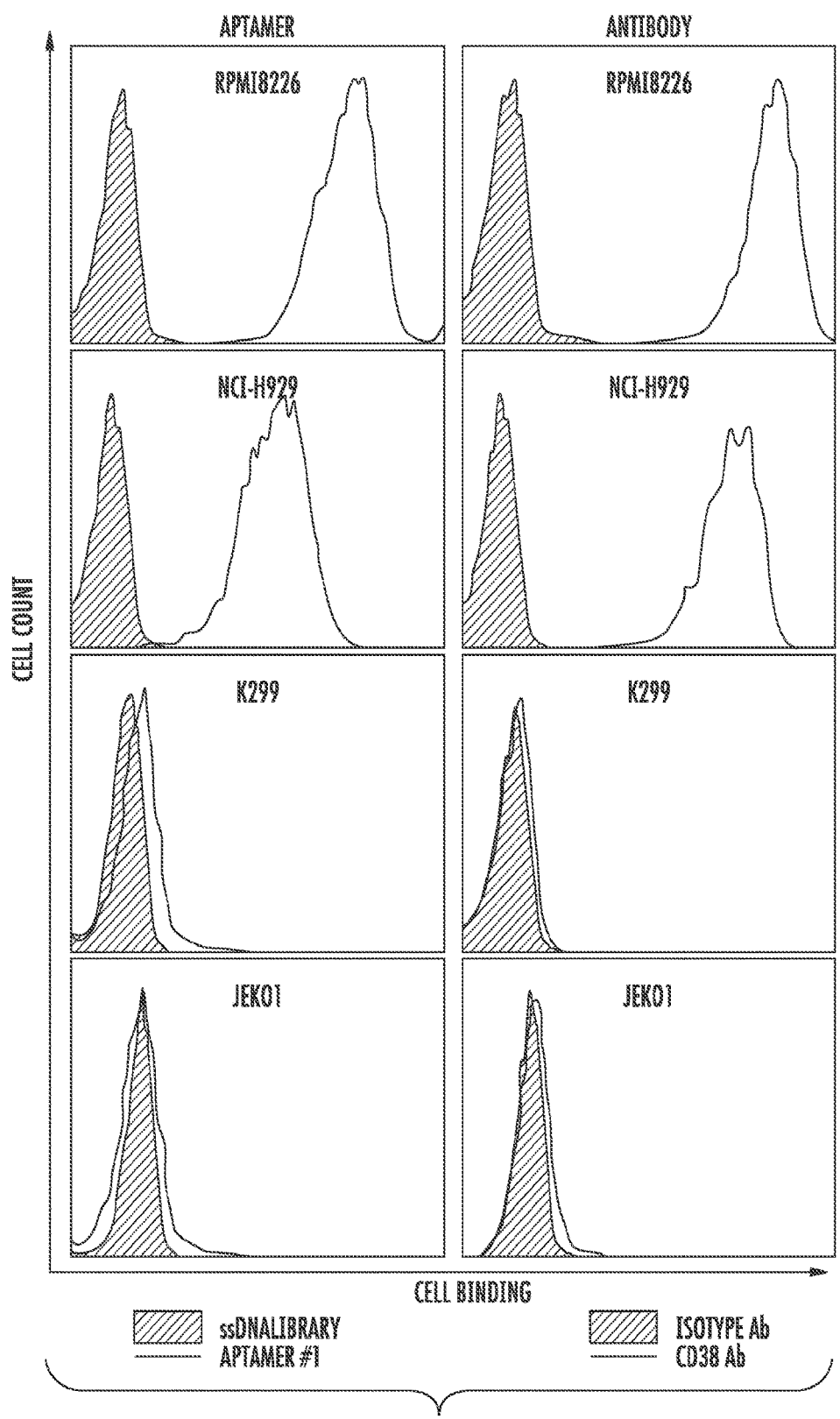
Figure 10D:
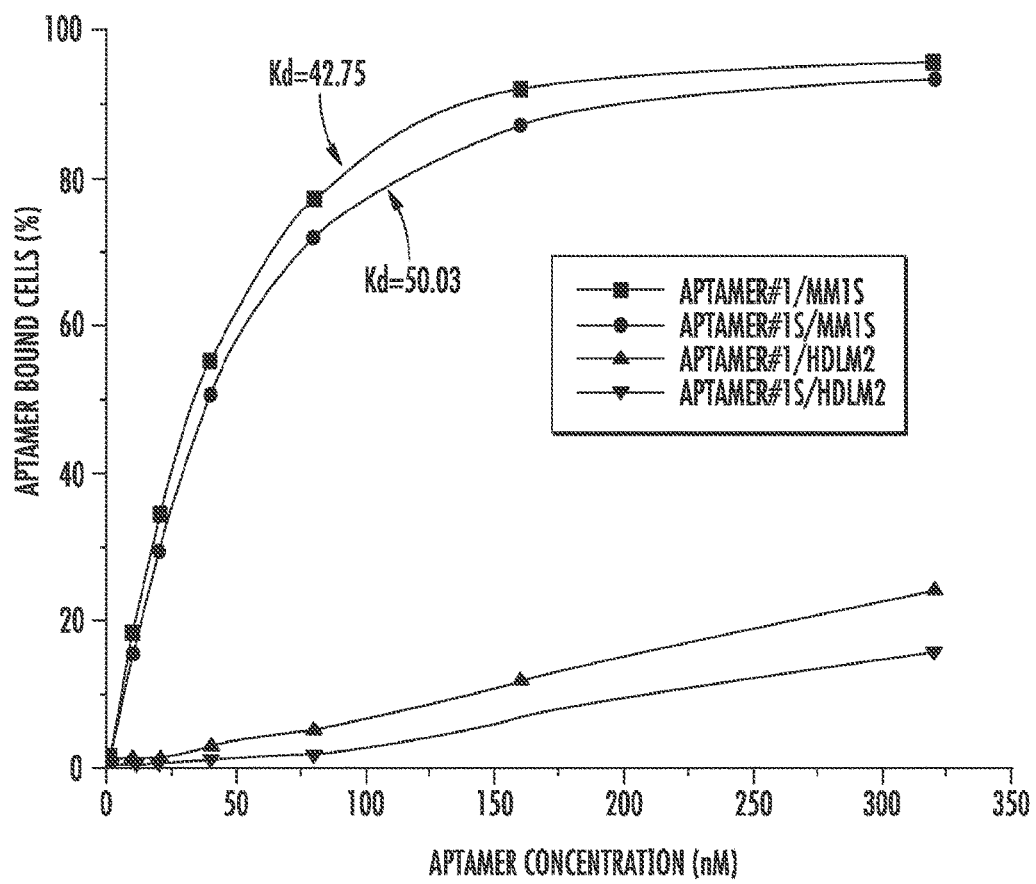
Figure 11:
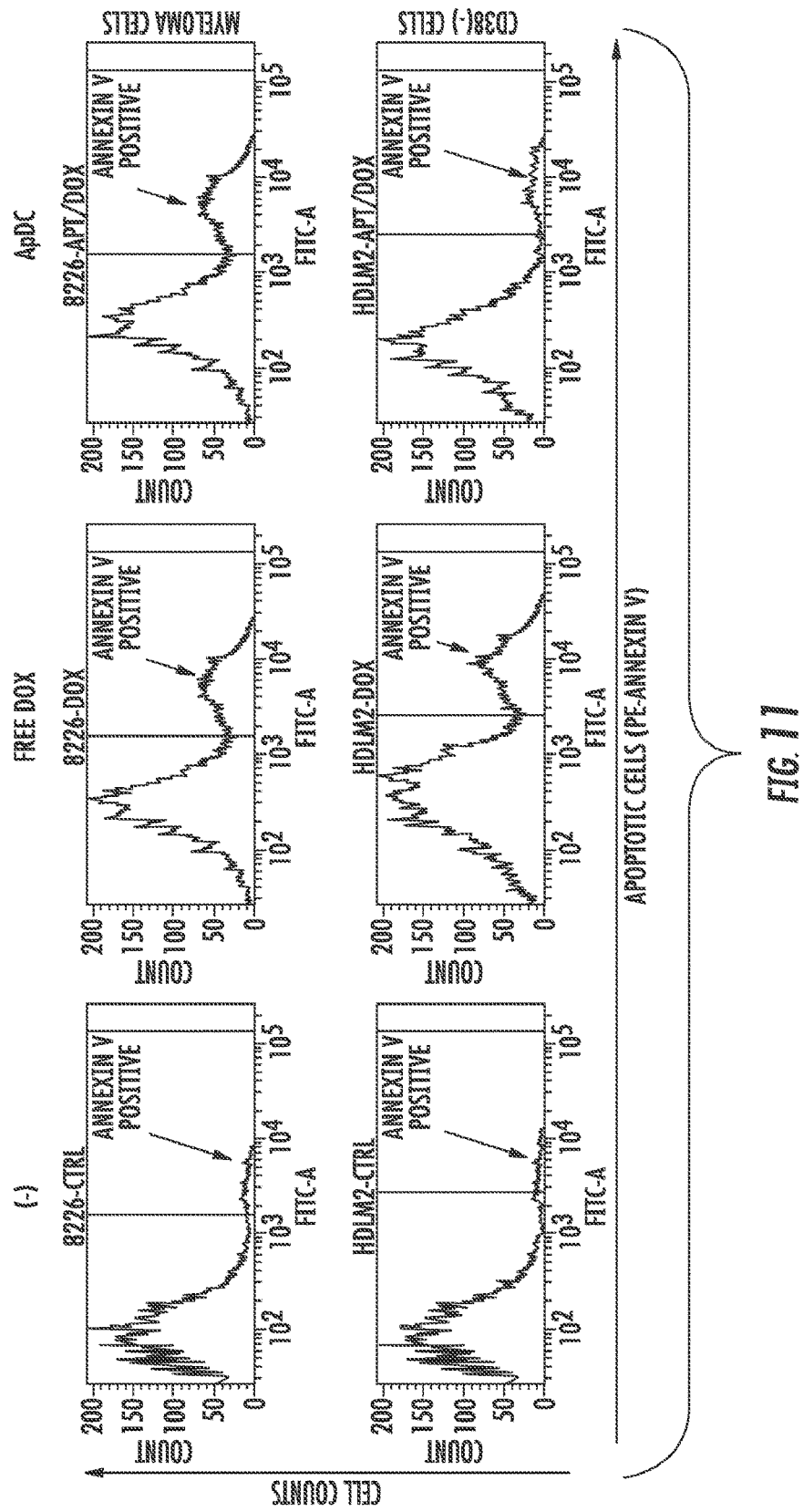
FIG. 11 shows the ApDC treatment induced apoptosis of MM cells, but had no effect on CD38(−) control cells, despite their similar sensitivity to free Dox and under the same treatment condition. Cultured MM cells and CD38(−) control cells were treated with ApDC, an equal amount of free Dox, or PBS vehicle. After cultured for 24 hr, cells were stained with FITC-labeled annexin V and apoptosis rates under each treatment condition were quantified by flow cytometry.

Selection and Characterization of MM Cell-Targeted and CD38-Specific ssDNA Aptamer To develop CD38-specific ssDNA aptamers that are also able to target MM cells, a hybrid SELEX process including 15 rounds of MM cell-based selection and 5 rounds of CD38 protein-based enrichment was carried out. Obtained aptamer sequences were determined by next generation sequencing. (FIG. 9A). The dominant Aptamer#1 accounts for 20.2% and Aptamer#2 for 19.36% respectively of total sequence reads. The top 20 sequences are comprised of 3 groups by clustal analysis and aptamers within each group show minimal variation (FIG. 9B). For example, Aptamer#1 and #4, Aptamer#2 and #8, Aptamer#7 and #19 only have one different nucleotide (FIG. 9C). Cell binding assays reveal that all three tested aptamer (#1, #2, and #7) specifically bound to MM cells (MM1S) and did not react to control cells (HDLM2). Among them, Aptamer#1 has the highest binding affinity and specificity (FIG. 10A, 10C) and its affinity Kd for MM1S cells is 42.75 (FIG. 10D). Therefore, the CD38#1 aptamer sequence was chosen for subsequent use. The 2nd structure of Aptamer#1 predicted with ValFold software was shown in FIG. 10B.

Figure 1D:
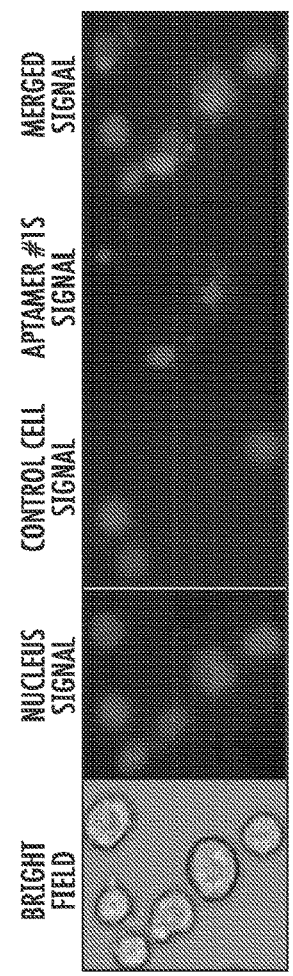
Figure 1B:
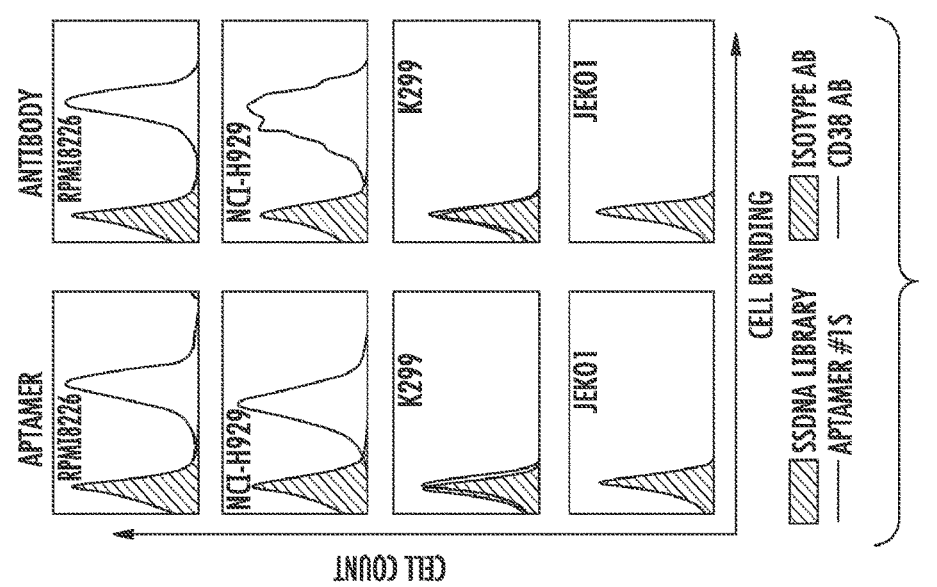

Notably, the full length of Aptamer#1 contains 40-mer core sequence and the fixed primer regions at both ends (FIG. 1A). To determine minimal functional sequence, CD38#1 aptamer was then truncated based on the predicted structure by ValFold and Pseudoviewer software. The truncated 61-mer Aptamer#1S inheriting the intact stem-loop structure and the 40-mer core sequence were synthesized and labeled with Cy3 fluorescent reporter for detection. Cell binding analysis demonstrated that the Aptamer#1S specifically targeted MM cells (MM1S) with a Kd=50.03 (FIG. 10D) similar to full length aptamer (Kd=42.75) and did not react to CD38-negative control cells (HDLM2). In contrast, the 40-mer core sequence lost cell binding capacity (FIG. 1A). Specificity of the Aptamer#1S was further confirmed in additional MM and control cells (FIG. 1B). To explore the binding target of aptamer, fresh cell lysates were incubated with Aptamer#1 and Aptamer#1S, the aptamer-bound proteins were separated on SDS-PAGE and probed with an anti-CD38 antibody as described under "Materials and Methods". Western blot confirmed that both aptamers specifically reacted to and immunoprecipitated cellular CD38 proteins from MM cells (MM1S). Since Aptamer#1S is smaller in size and may have higher potential for in vivo tissue penetration, it was selected for further validation studies. A cell mixture composed of both cultured MM cells and control cells, which was CD38 negative and pre-stained in green fluorescence for identification, were treated with Cy3-labeled aptamer#1S. Fluorescence microscopy revealed that the aptamer selectively targeted MM cells (red fluorescence) and did not react to control cells (pre-stained in green) in the same mixture (FIG. 1D). In addition, the presence of strong intracellular signals indicated that the aptamer was internalized into the MM cells, showing its potential for intracellular drug delivery.

Figure 2A:
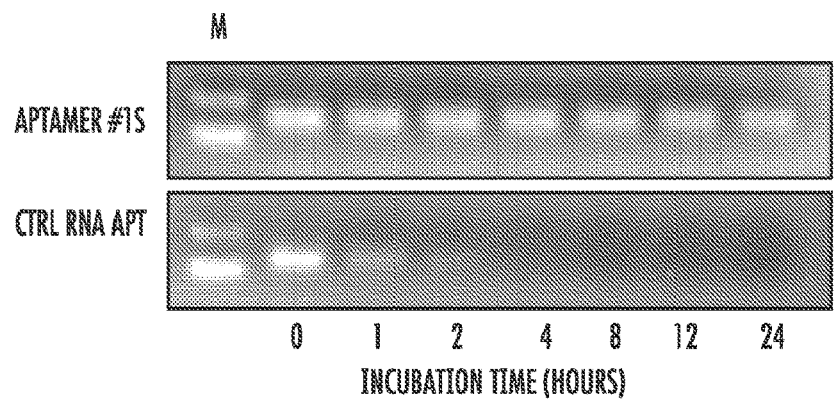
FIG. 2 shows aptamer biostability of Aptamer#1S (SEQ ID NO: 2) in vitro and in vivo. (A) ssDNA-based Aptamer#1S and control RNA-based aptamers were incubated with human serum and their biostability was assessed by agar gel electrophoresis at the indicated time intervals. (B) Cy5.5-labeled Aptamer#1S was injected into mice bearing two tumors derived from luciferase-tagged PRMI8226GL (CD38+) and K299GL (CD38-) cell lines. Bioluminescence (tumor) and fluorescence (aptamer) were evaluated with Xenogen IVIS imaging system.
Figure 2B:
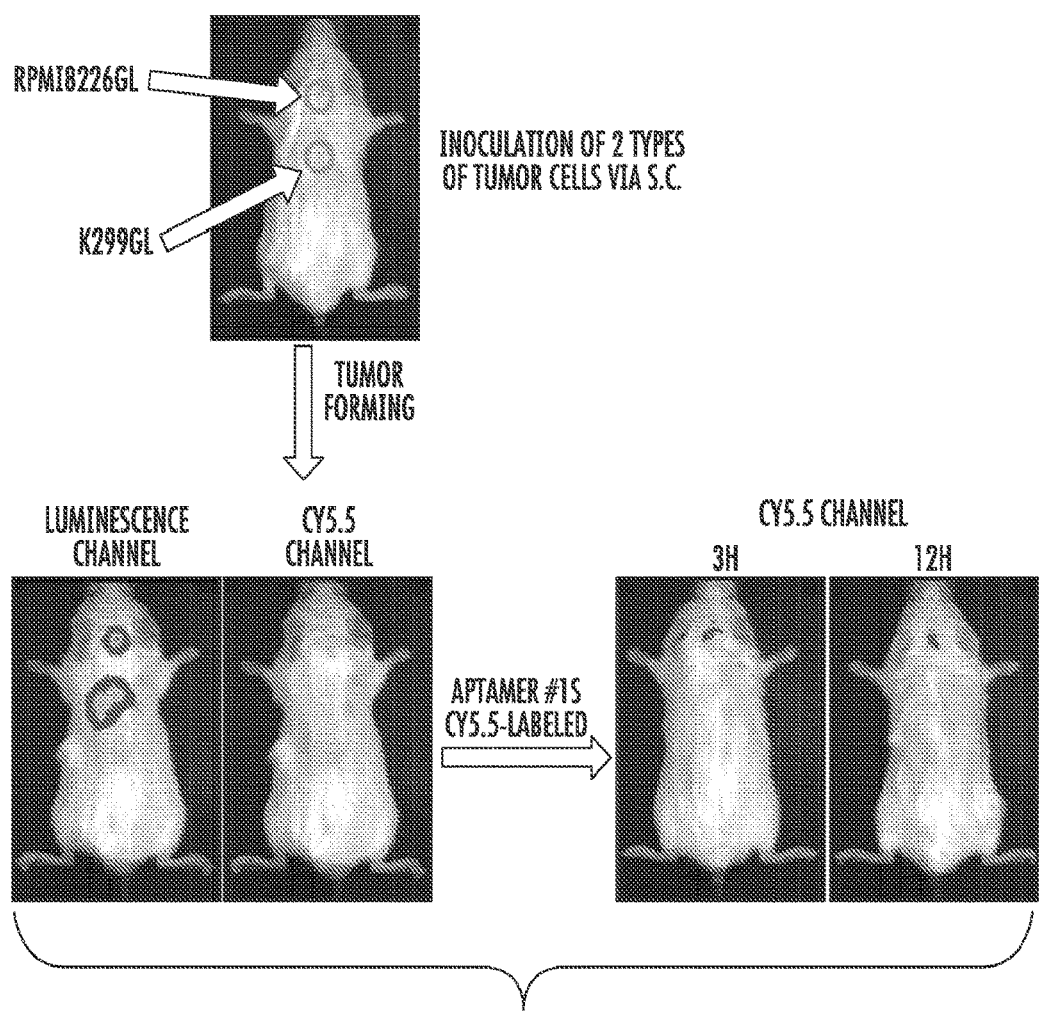

Biostability is a major concern for in vivo applications of aptamers. To this end, the Aptamer#1S and a control RNA-based aptamer of a similar length were incubated in human serum at 37° C. to mimic the in vivo conditions. Residual aptamer products were then collected at different time points and analyzed by gel electrophoresis. FIG. 2A reveals that the Aptamer#1S were stable over 24 h while the RNA-based aptamers were completely degraded within 2 h. For in vivo validation, the Aptamer#1S was labeled with Cy5.5 reporter and systemically administered into mice bearing xenograft tumors of MM (RPMI8226GL) and lymphoma (K299GL). The development of both tumors was confirmed by detecting luminescence signals generated by the tumor cells expressing luciferase (FIG. 2B). Whole body fluorescent imaging scan revealed that Aptamer#1S specifically targeted and was selectively accumulated in MM tumor, but not in control tumor present in the same mouse. The specific imaging signals lasted up to 12 h post systemic administration. These results confirm that the aptamer#1S was biostable and able to selectively target MM tumor, indicating its suitability to guide targeted drug delivery in vivo.

Development and Characterization of a MM Cell-Specific Aptamer-Drug Conjugate (ApDC)

For targeted therapy, the ideal delivery system should be able to carry high payload of therapeutic drug, be stable in vivo for systemic delivery, specifically target tumor cells of interest, and, more importantly, selectively release drug payload within the target cells for therapeutic effect. To this end, ApDC was formulated by synthesizing the validated CD38-specific aptamer#1S with an additional CG repeat sequence at 5' end for drug loading. Secondary structure of the formulated ApDC was predicted by ValFold and Pseudoviewer software and showed in FIG. 3A. The CG repeat sequence can form a cargo structure and incorporate multiple doxorubicin (DOX) molecules through a non-covalent reaction (Bagalkot, V., Farokhzad, O. C., Langer, R., and Jon, S. 2006. An aptamer-doxorubicin physical conjugate as a novel targeted drug-delivery platform. Angew Chem Int Ed Engl 45:8149-8152; Meng, L., Yang, L., Zhao, X., Zhang, L., Zhu, H., Liu, C., and Tan, W. 2012. Targeted delivery of chemotherapy agents using a liver cancer-specific aptamer. PLoS One 7:e33434). In addition, two CG repeats were also present within aptamer sequence for DOX incorporation.

Figure 3A:
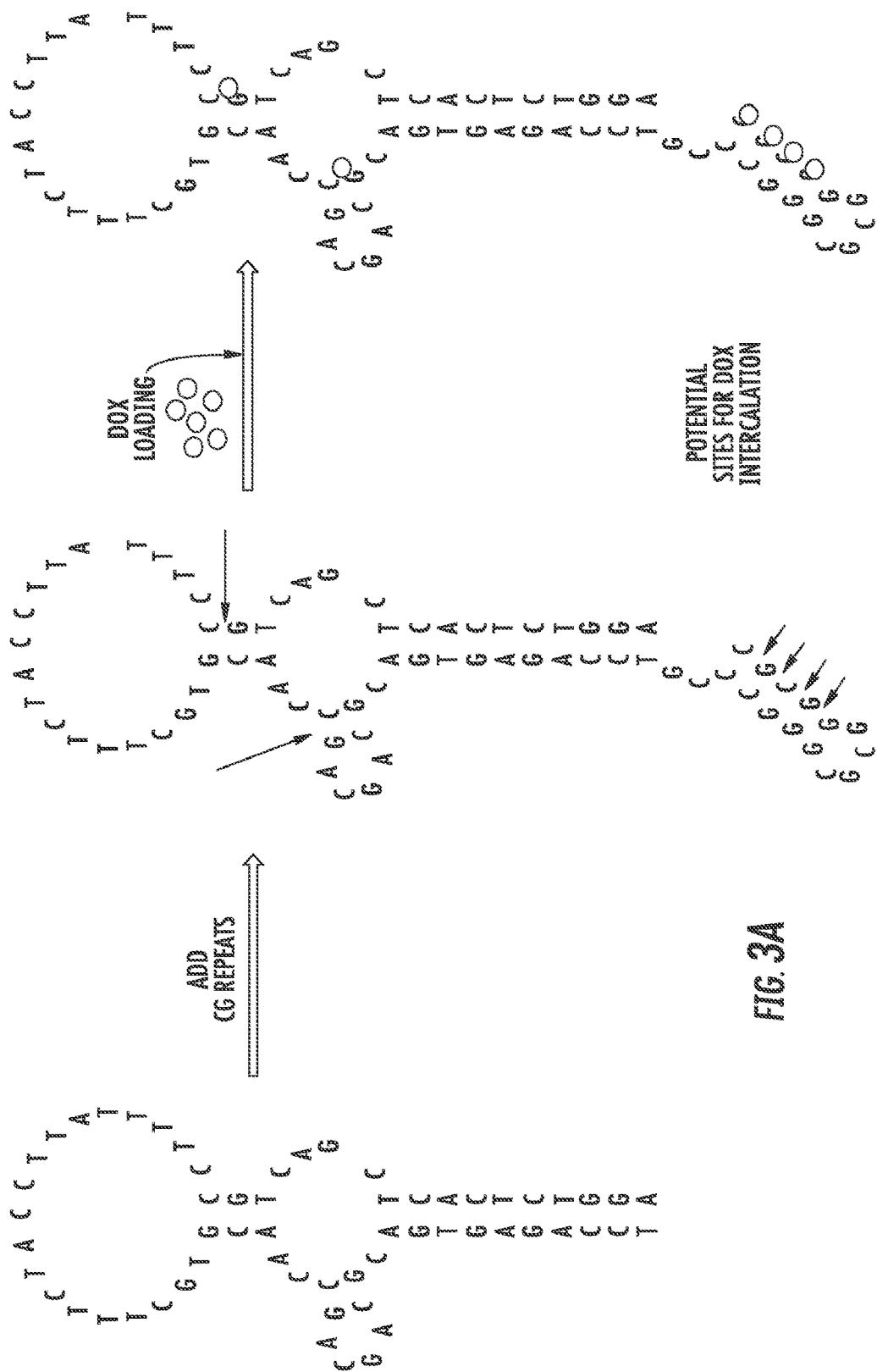
FIG. 3 shows formation of aptamer drug-conjugates (ApDC) using Aptamer #1S (SEQ ID NO: 2) and doxorubicin (DOX) drug and capacity of the formed ApDCs for drug loading and release. (A) Schematic representation of aptamer modification and DOX loading. (B) Determination of DOX loading capacity of Aptamer#1S with CG-Cargo sequence. Data are the representative of three independent experiments. Bars correspond to mean±SD. (C) Synthesized aptamer/CG-Cargo sequence is indispensable for carrying and pH-triggered release of DOX. DOX loading capacity was compared in Aptamer#1S alone, CG-Cargo sequence alone, and Aptamer#1S/CG-Cargo. Data are the representative of three independent experiments depicted as mean±SD. (D) The intercalation of DOX into aptamer was confirmed by incubating indicated samples with DNase I and measuring fluorescence of free DOX at 590 nm. (E) ApDC was heated from 25° C. to 95° C., and its DOX release was measured. Data represent the fluorescence density relative to free DOX control. (F) ApDC was incubated in human serum and fluorescence relative to free DOX was measured at 590 nm over 24 hours. Data are the representative of three independent experiments depicted as mean±SD. (G) ApDC was incubated in binding buffer has pH values ranging from 7.4 to 1 and fluorescence relative to free DOX was monitored at 590 nm continuously. Data are the representative of three independent experiments depicted as mean±SD.
Figure 3B:
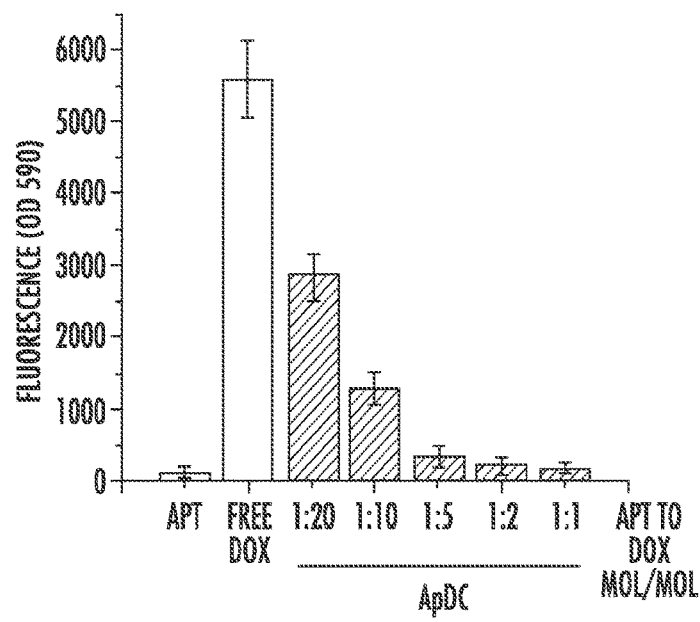
Figure 3C:
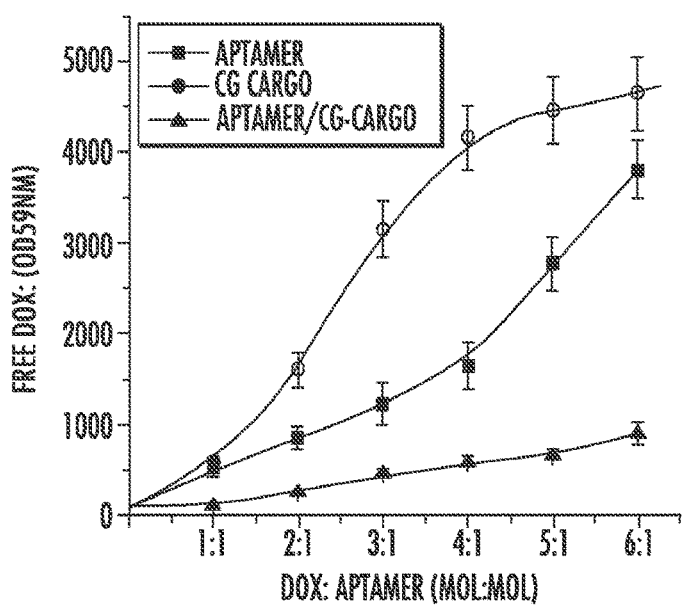
Figure 3D:
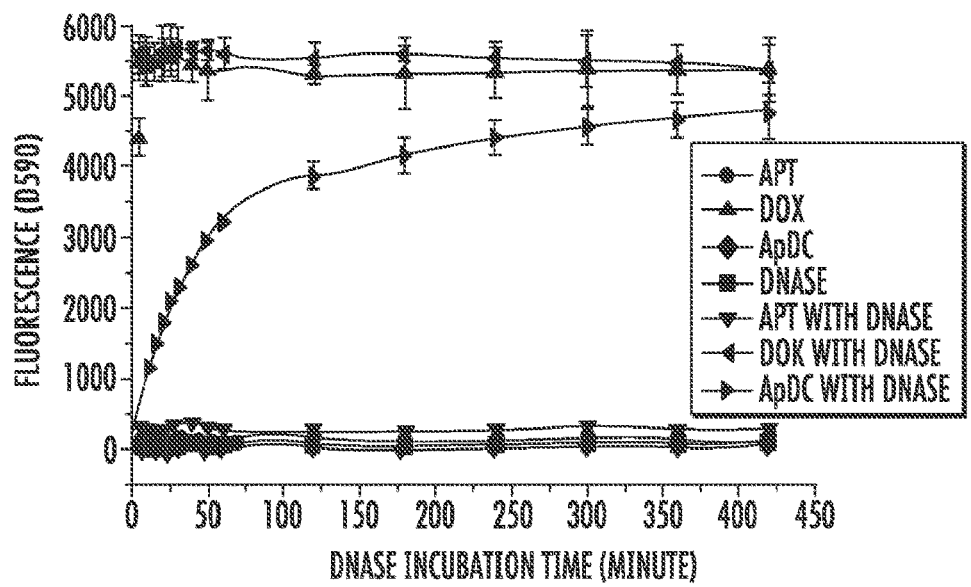
Figure 3E:
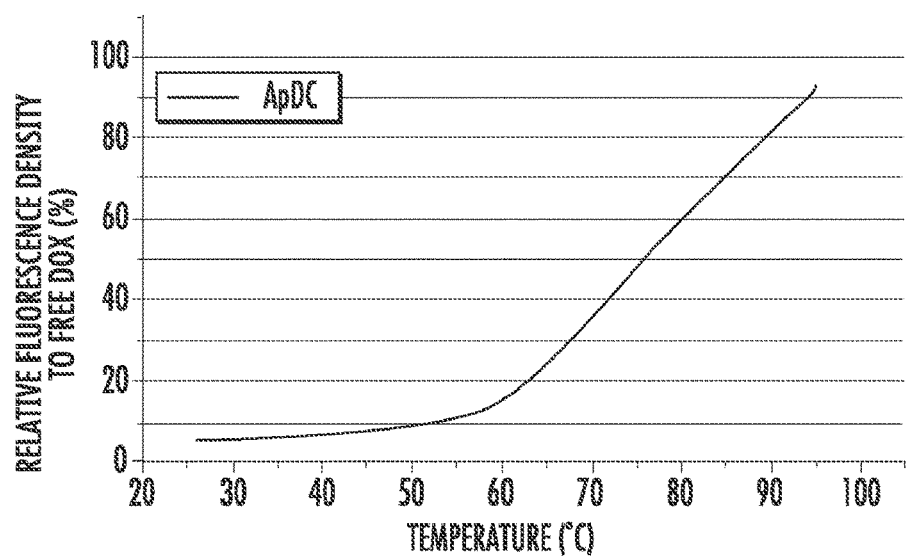

To evaluate drug loading capacity, the synthesized aptamer/CG-Cargo was heated and cooled down in the presence of different molar ratios of aptamer to DOX to form the ApDC as indicated in FIG. 3B. Because free DOX is fluorescent and its incorporated form is optically silent due to quenching effect of ApDC, the reaction was monitored using a microplate reader (Em=590 nm). FIG. 3B shows that each ApDC molecule could almost completely incorporate five DOX payloads (mol/mol) with no free DOX left in the reaction. Therefore, the ApDC formed at 1:5 molar ratio of aptamer to DOX was used for subsequent therapy study. The CG repeat cargo structure alone or aptamer sequence alone showed very limited drug loading capacity (FIG. 3C). To confirm DOX intercalation, the ApDC were treated with DNase I and released free DOX was monitored by measuring fluorescence changes in reactions. FIG. 3D revealed that DNase treatment resulted in release of free DOX from the ApDC, but no change was seen in reactions composed of aptamer alone or free DOX alone.

Figure 3F:
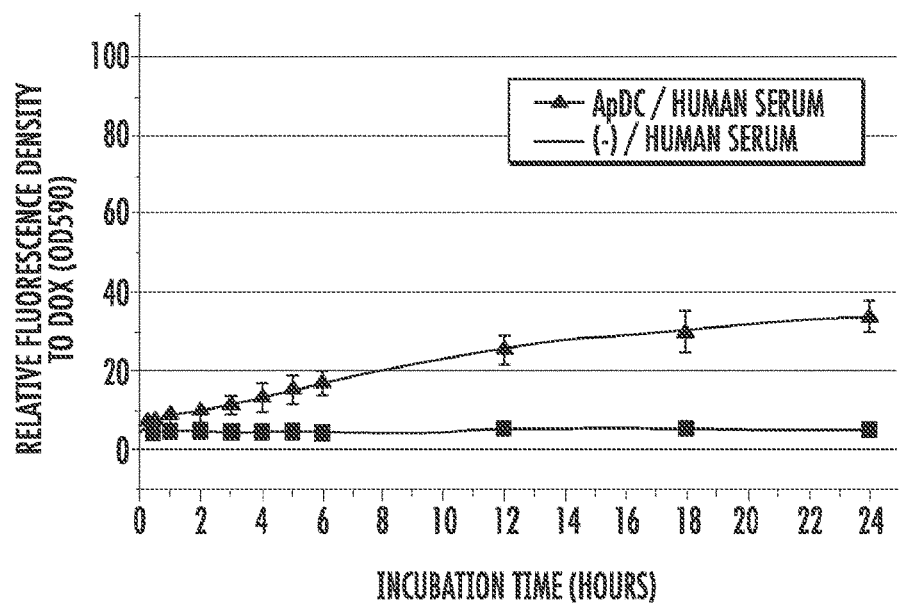
Figure 3G:
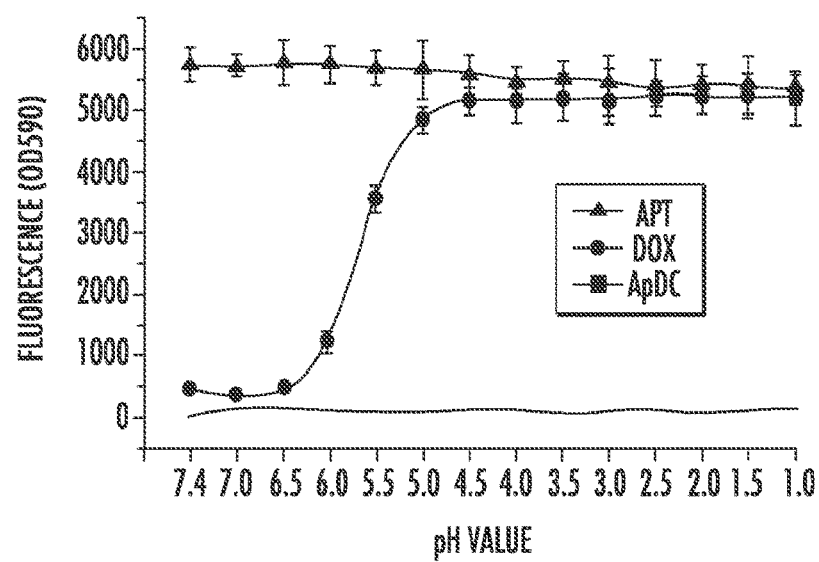

For biostability analysis, ApDC were incubated in culture medium at different temperatures for 1 h and released free DOX was monitored. As showed in FIG. 3E, the formed ApDC was stable at temperatures <50° C. In addition, ApDC were incubated in human serum at 37° C. and the released free DOX was kinetically monitored. The ApDC were stable in serum, retaining more than 60% of its DOX payload after 24 h incubation (FIG. 3F). For therapeutic effect, the ApDC need to be able to rapidly release drug payload within cells of interest. Since the final destination of ApDC will be cell lysosomes that have a low pH environment (Misinzo, G., Delputte, P. L., and Nauwynck, H. J. 2008. Inhibition of endosome-lysosome system acidification enhances porcine circovirus 2 infection of porcine epithelial cells. J Virol 82:1128-1135; Boyacioglu, O., Stuart, C. H., Kulik, G., and Gmeiner, W. H. 2013. Dimeric DNA Aptamer Complexes for High-capacity-targeted Drug Delivery Using pH-sensitive Covalent Linkages. Mol Ther Nucleic Acids 2:e107), ApDC was incubated in culture medium at different pH for 30 min and release of free DOX was monitored. Resultant fluorescent changes in reactions indicate that ApDC rapidly released their DOX payload when pH dropped below 6.0 and reached maximal at pH 5.0 (FIG. 3G). These results show that the ApDC is able to carry high DOX payloads under biological and physiological conditions, and can rapidly release DOX payloads under a low pH condition that is seen in cell lysosome microenvironment.

ApDC Specifically Targeted MM Cells and Selectively Induced MM Cell Apoptosis

Figure 4A:
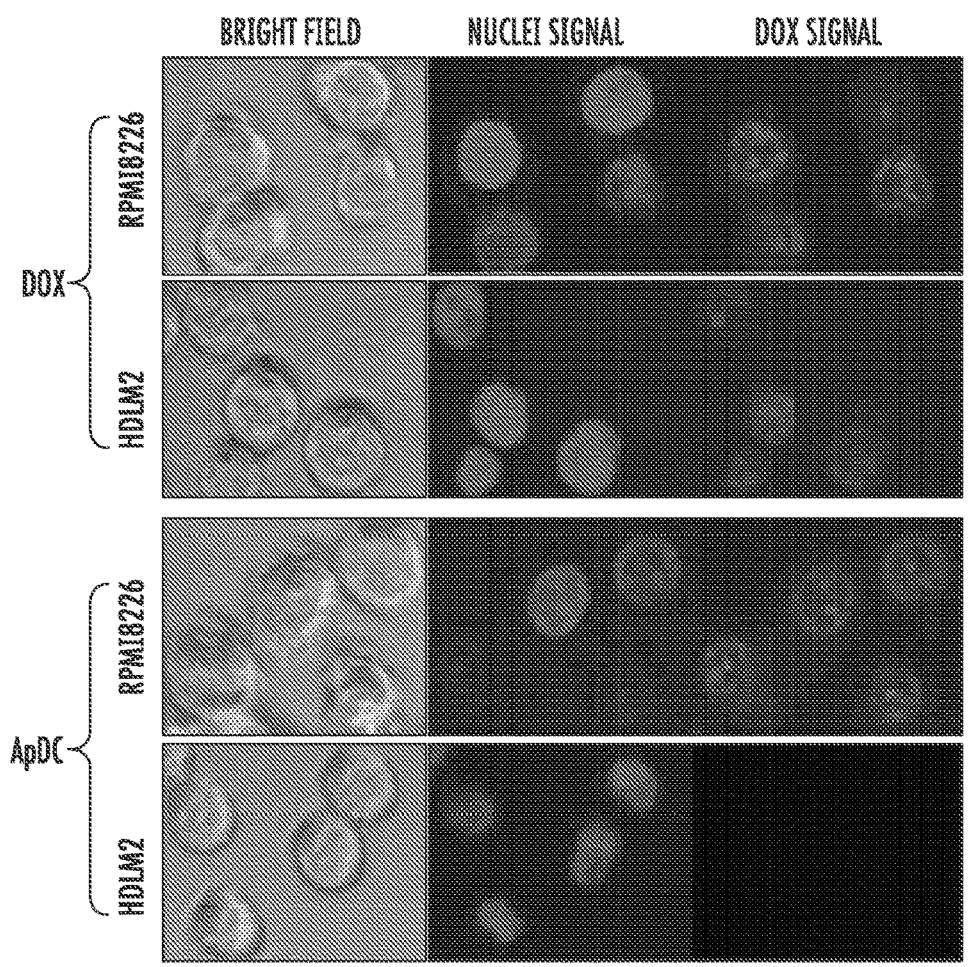
FIG. 4 shows selective uptake of CD38-specific ApDC induces cytotoxicity in CD38+ cells. (A) RPMI8226 (CD38+) and HDLM2 (CD38−) cells were incubated with free DOX or ApDC and cell fluorescence was examined by confocal microscopy. (B) RPMI8226 and HDLM2 cells were treated with equal molar amounts of aptamer, free DOX, or ApDC and cell lysates analyzed by western blot for changes in the level of cleaved caspase-3. (C) CD38+ MM cells (upper panel) and CD38− cells (lower panel) were treated with equal molar amounts of aptamer, free DOX, or ApDC and cell apoptosis was determined by Annexin V staining. Data are the representative of three independent experiments. Bars correspond to mean±SD. (D) RPMI8226 and HDLM2 cells were pre-treated with vehicle control (PBS), equal molar amounts of free DOX, or ApDC for 2 hours, plated in soft agar, and their colony forming abilities were analyzed following incubation for 2 weeks. Representative pictures from each group are shown (upper panel) and data are the representative of three independent experiments. Bars correspond to mean±SD (lower panel).

To validate the aptamer-guided drug delivery, MM cells (RPMI8226) and control cells (HDLM2) were treated with ApDC, as well as equal molar free DOX as a control for 2 h. Cells were washed and intracellular drug delivery was then determined by detecting free DOX fluorescence under confocal microscopy since the incorporated DOX in ApDC was optical silent. The ApDC treatment resulted in selective DOX delivery into MM cells, but no DOX signals were seen in control cells under the same treatment conditions. In contrast, non-specific intracellular drug accumulation of free DOX was observed in both MM and control cells (FIG. 4A).

Figure 4B:
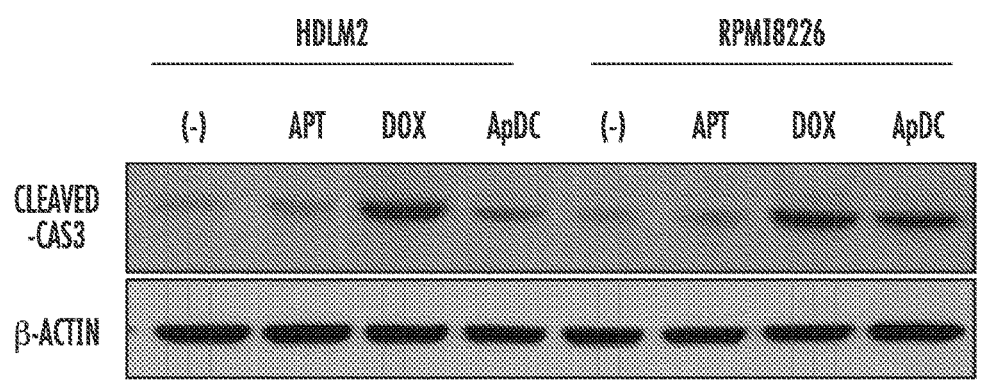

To examine therapeutic effect, MM cells (RPMI8226) and control cells (HDLM2) were treated with ApDC or equal molar free DOX for 2 h and further cultured in fresh medium for 24 h. Resultant changes in cell apoptosis were monitored by cleavage of cellular caspase 3 proteins, a hallmark of apoptotic machinery. Western blot assay revealed that ApDC treatment selectively induced apoptosis MM cells, but had minimal apoptotic effect on control cells (FIG. 4B). In contrast, free DOX alone showed similar effect on cellular apoptosis of both cells. For further validation, additional cultured cells were treated and stained with Annexin V and apoptotic cells were counted by flow cytometry. ApDC induced apoptosis of MM cells and has little effect on CD38-negative cells although free DOX showed similar effect on all tested cells under the same treatment conditions (FIG. 4C). Moreover, the treated cells (RPMI8226 and HDLM2) were also cultured in fresh soft agar plates for 2 weeks and formed colonies were counted. FIG. 4D reveal that ApDC treatment resulted in significant reduction of MM cell colony formation but had little effect on off-target cells.

Figure 5A:
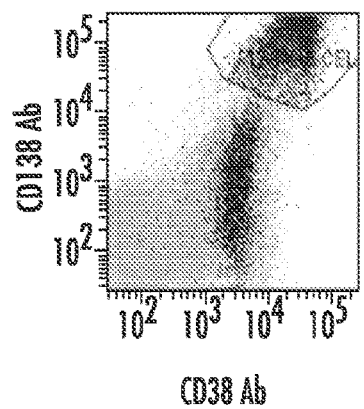
FIG. 5 shows CD38-specific ApDC induced selective cytotoxicity in patient-derived MM cells. (A) Mononuclear cells isolated from bone marrow aspirates of MM patients were co-stained with anti-CD138 and anti-CD38 antibodies and analyzed by flow cytometry. (B) A diagram of patient-derived mononuclear cell separation by FACS based on their CD138 expression. Post-separation sample purity is shown in two respective scatter plots. (C) CD138+ and CD138− cells isolated from 4 MM patient bone marrow aspirates were treated with equal molar amounts of aptamer, free DOX, or ApDC and induced apoptosis was determined by flow cytometry with Annxin V stains (left panel). Right panel shows the average of total 6 patient samples and data are shown as mean±SD.
Figure 5B:
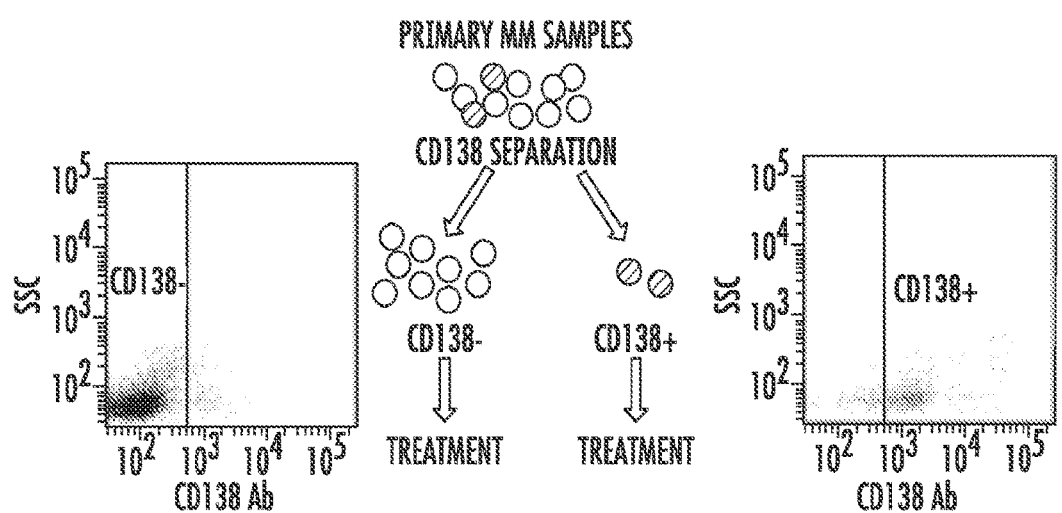
Figure 5C:
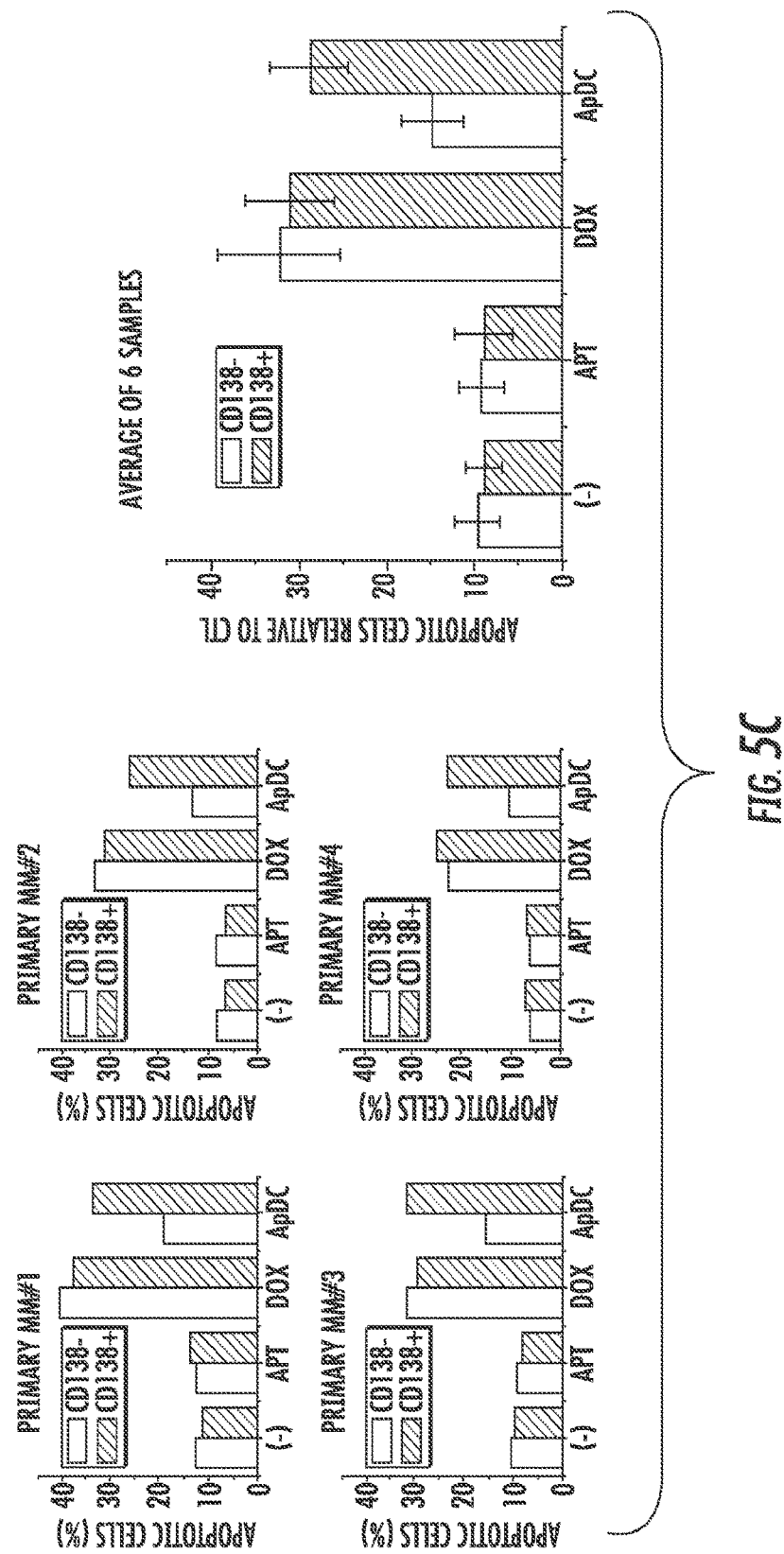

Next, marrow specimens of MM patients were collected and the presence of MM cells were confirmed staining cell surface CD38 and CD138 biomarkers by antibodies (FIG. 5A). Subsequently, primary MM cells were separated from background marrow mononuclear cells by cell CD138 staining to avoid any effect on cell surface CD38 (FIG. 5B). Cells were treated with ApDC or equal molar free DOX, and changes in cell apoptosis were then quantified by flow cytometry with Annexin staining. As shown in FIG. 5C, ApDC treatment triggered apoptosis of primary MM cells and had minimal effect on background marrow cells from the same patients, although both MM and marrow cells showed similar sensitivity to free DOX treatment.

Figure 6D:
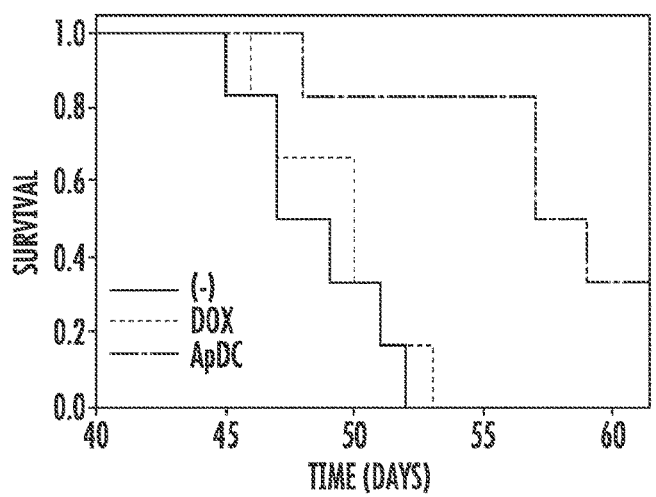
FIG. 6 shows treatment of MM-bearing mice with CD38-specific ApDC is associated with retarded tumor growth and improved survival. (A) A pictorial representation of tumor inoculation and treatment schedule, with tumor-bearing mice treated every 2 days for 24 days, beginning from Day 6. (B) Mouse tumor burden (based on whole-body bioluminescence imaging) was analyzed and data are shown as mean±SD (n=6). (C) Mice were imaged at day 30 and results are shown for all animals. (D) Survival curves of MM-bearing mice with different treatments are shown. (E) Cells isolated from tumor tissues were examined by fluorescence microscopy for GFP expression of MM cells. (F) Cells isolated from tumor tissues were analyzed by immunohistochemical stain for expression of human CD38, Ig λ light chain, and Ig κ light chain. (G) Immunocompetent mice were treated with equal molar amounts of aptamer, free DOX, or ApDC and serum levels of mouse inflammatory cytokines (IFNγ, IL-1β, IL-2, IL-6, and TNFα) were quantified at time points indicated. Data are shown as mean±SD. (n=6)

Systemic ApDC Treatment Inhibited Orthotopic MM Tumor Growth and Prolonged Mouse Survival For in vivo therapy study, orthotopic MM tumors were established by inoculating mice with GFP and luciferase-expressing human MM cells (RPMI8226GL) through bilateral tibial implantation as reported previously (Feng, Y, Wen, J., Mike, P., Choi, D. S., Eshoa, C., Shi, Z. Z., Zu, Y, and Chang, C. C. 2010. Bone marrow stromal cells from myeloma patients support the growth of myeloma stem cells. Stem Cells Dev 19:1289-1296). Mice were then treated with systemic administrations of ApDC (0.5 mg/kg of Dox payload, a sub-toxic concentration to eliminate potential side effect) or equal molar free Dox alone at day 6, and treatments were subsequently repeated every other day for total 13 times of treatment (FIG. 6A). Changes in MM tumor sizes were monitored by whole-body bioluminescence imaging scans every 6 days and summarized in FIG. 6B. Whole-body images at day 36 were showed in FIG. 6C. For the survival rate study, mice were observed for up to 60 days and Kaplan-Meier survival analyses of mice with different treatments was conducted. The ApDC treatment significantly improved survival rate of mice bearing orthotopic MM tumors (FIG. 6D). However, under the same treatment condition equal molar free Dox had no effect on mouse survival in comparing to non-treatment group. These findings demonstrate that the ApDC was able to deliver DOX specifically to MM tumor for targeted therapy.

Figure 6E:
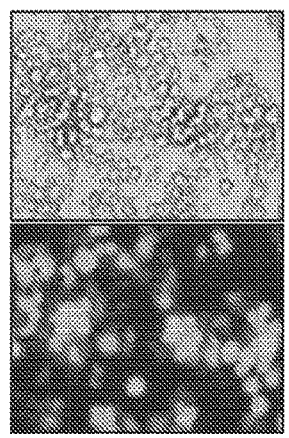
Figure 6F:
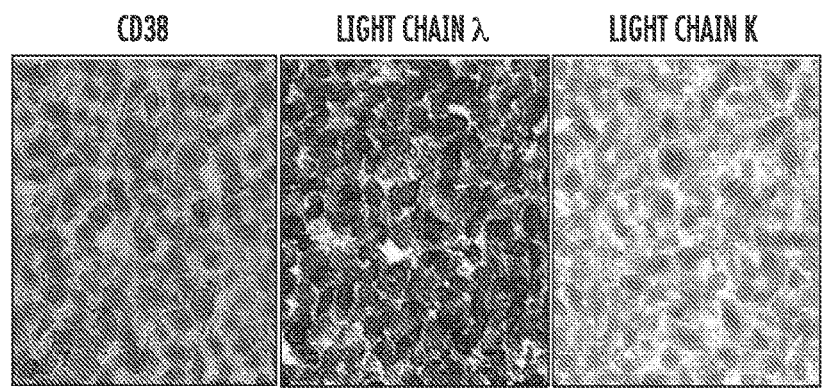
Figure 6G:
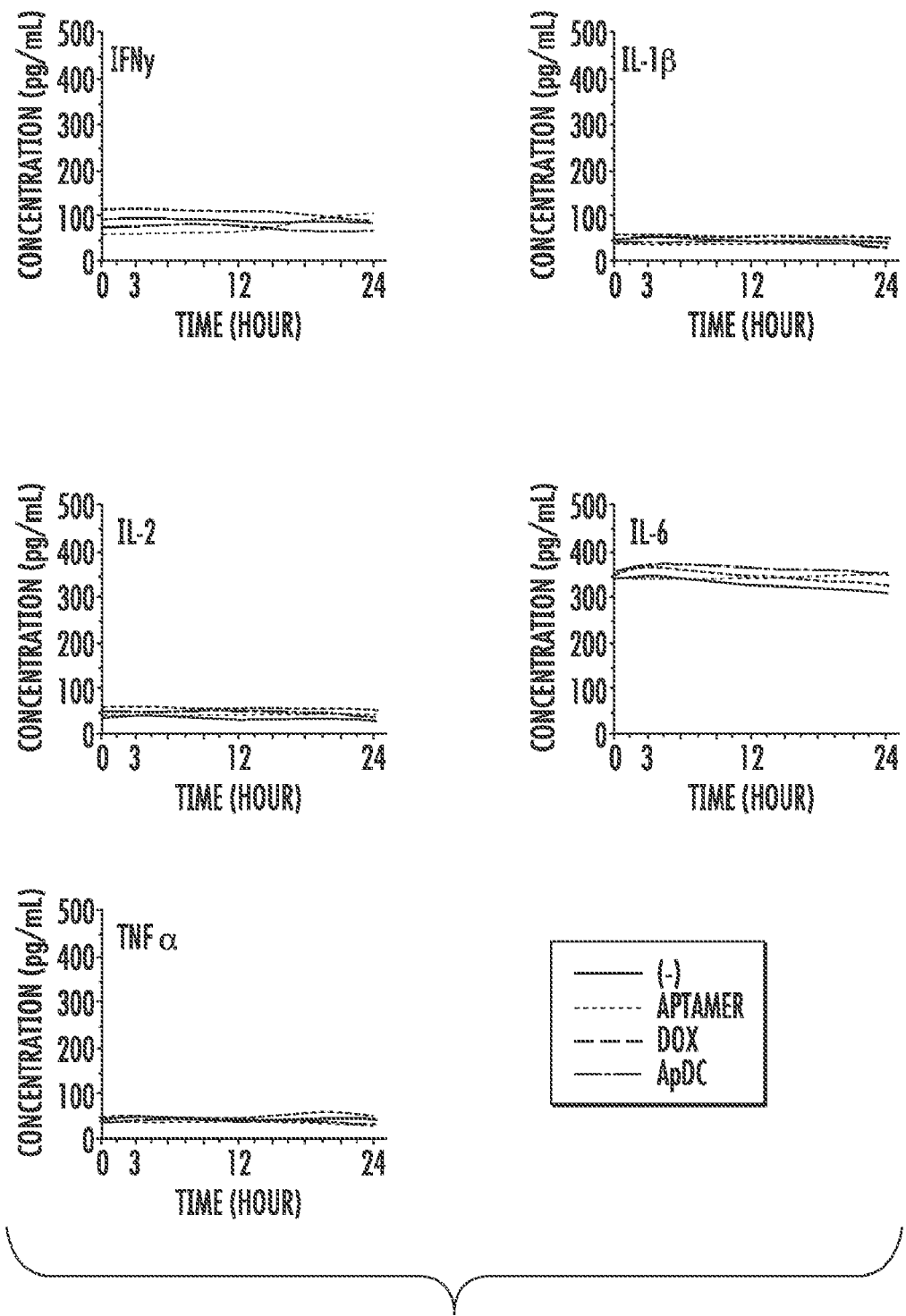

For histological confirmation, fresh cells from orthotopic MM tumors were collected and cellular GFP expression was examined under fluorescent microscope (FIG. 6E). Moreover, tumor tissues were fixed and immunostained, revealing Ig lambda light chain-restricted MM tumor cells (FIG. 6F). To rule out potential side effects, healthy immunocompetent mice were systemically administered with ApDC and control treatments at the same dose as described above. Changes in serum inflammatory cytokines, including IFNγ, IL-1β, IL-2, IL-6, and TNFα, were evaluated at 3, 12, and 24 hr post treatments. As showed in FIG. 6G, ApDC treatment did not induce systemic inflammatory reactions in comparing to control treatments (FIG. 6G). These findings demonstrate suitability of the ApDC for in vivo targeted MM therapy since it has little or no non-specific inflammatory effects.

MATERIALS and METHODS

Cell Culture and Reagents

Human myeloma cell lines RPMI8226, NCI-H929 were purchased from American Type Cell Culture (ATCC, Manassas, Va.). Dexamethasone-sensitive (MM1S) and resistant (MM1R) cell lines were kindly provided by Dr. Steven Rosen (Northwestern University, Chicago, Ill.). Non-MM cell lines (HDLM2, K299, Jeko1, and L428) were purchased from ATCC. RPMI8226 GL and K299 GL cell lines concomitantly expressing GFP and luciferase were generated according to the manufacturer's protocol by transfection with a pLenti6/V5 plasmid (Life Technologies, Grand Island, N.Y.) that contained a green fluorescent protein-luciferase fusion gene (Wen, J., Tao, W., Kuiatse, I., Lin, P., Feng, Y., Jones, R. J., Orlowski, R. Z., and Zu, Y. 2014. Dynamic balance of multiple myeloma clonogenic side population cell percentages controlled by environmental conditions. Int J Cancer). All cell lines were grown in RPMI 1640 (Life Technologies) culture medium supplemented with 10% fetal bovine serum (FBS, Atlanta Biologicals, Atlanta, Ga.), 100 U/mL penicillin, and 100 μg/mL streptomycin (Thermo Fisher Scientific, Houston, Tex.), as previously reported (Wen, J., Feng, Y., Bjorklund, C. C., Wang, M., Orlowski, R. Z., Shi, Z. Z., Liao, B., O'Hare, J., Zu, Y, Schally, A. V., et al. 2011. Luteinizing Hormone-Releasing Hormone (LHRH)-I antagonist cetrorelix inhibits myeloma cell growth in vitro and in vivo. Mol Cancer Ther 10:148-158). Primary bone marrow mononuclear cells were isolated by density gradient centrifugation using Ficoll-Paque (GE Healthcare, Pittsburgh, Pa.) under a protocol approved by the Houston Methodist Research Institute IRB as reported previously (Wen, J., Li, H., Tao, W., Savoldo, B., Foglesong, J. A., King, L. C., Zu, Y, and Chang, C. C. 2014. High throughput quantitative reverse transcription PCR assays revealing over-expression of cancer testis antigen genes in multiple myeloma stem cell-like side population cells. Br J Haematol 166:711-719). All reagents, unless otherwise stated, were purchased from Sigma-Aldrich Co. (St. Louis, Mo.). SELEX washing buffer and binding buffer for aptamers were prepared as reported (Sefah, K., Shangguan, D., Xiong, X., O'Donoghue, M. B., and Tan, W. 2010. Development of DNA aptamers using Cell-SELEX. Nat Protoc 5:1169-1185).

DNA Library and Primers Primers and DNA library were synthesized and purified by Integrated DNA Technologies Inc. (Coralville, Iowa) as reported (45). The DNA library was constructed from oligonucleotide sequences based on the following generic sequence: 5'-ATCCAGAGT-GACGCAGCA-N(40)-TGGACACGGTGGCTTAGT-3' (SEQ ID NO: 3), where N represents a randomized nucleotide (A, G, C, or T). Cy3-labeled 5' primer (5'-Cy3-ATC-CAGAGTGACGCAGCA-3' SEQ ID NO: 4) and biotin-labeled 3' primer (5'-Biotin-ACTAAGCCACCGTGTCCA-3' SEQ ID NO: 5) were used in the PCR process for the synthesis of double-labeled, double-stranded DNA molecules (Sefah, K., Shangguan, D., Xiong, X., O'Donoghue, M. B., and Tan, W. 2010. Development of DNA aptamers using Cell-SELEX. Nat Protoc 5:1169-1185).

Hybrid SELEX Process

The hybrid SELEX process combined cell SELEX and protein SELEX. Cell SELEX was performed using CD38+ (MM1S) and CD38− (HDLM2) cells. Protein SELEX was performed using the extracellular component of human recombinant CD38 protein (Life Technologies) affinity column, as described (Navani, N. K., Mok, W. K., and Yingfu, L. 2009. In vitro selection of protein-binding DNA aptamers as ligands for biosensing applications. Methods Mol Biol 504:399-415). To monitor the enrichment of aptamer candidates after each round of selection, the Cy3-labeled ssDNA pool was incubated with CD38-positive and negative cells and Cy3 fluorescence was determined with flow cytometry (LSR II, BD Biosciences, San Jose, Calif.). Following 20 rounds of selection (15 rounds of cell SELEX and 5 rounds of protein SELEX), final ssDNA pool was PCR-amplified with unmodified primers, purified with a ChargeSwitch PCR Clean-Up Kit (Life Technologies), and submitted for next-generation sequencing (LC Sciences LLC, Houston, Tex.) (Akitomi, J., Kato, S., Yoshida, Y, Horii, K., Furuichi, M., and Waga, I. 2011. ValFold: Program for the aptamer truncation process. Bioinformation 7:38-40).

Aptamer Screening and Truncation

The top-20 enriched aptamer sequences were synthesized to include Cy3 modification and their affinity and specificity analyzed by flow cytometry. Aptamer#1S was derived by truncating Aptamer#1 based on ValFold software structural prediction (VALWAY Technology Center, NEC Soft Ltd., Tokyo, Japan) (Navani, N. K., Mok, W. K., and Yingfu, L. 2009. In vitro selection of protein-binding DNA aptamers as ligands for biosensing applications. Methods Mol Biol 504: 399-415).

Cell Staining Procedures

For aptamer staining, cells were stained with Cy3-labeled aptamer at 50 nmol/L (for flow cytometry analysis) or 100 nmol/L (for fluorescence microscopy, Olympus America, Melville, N.Y.) for 30 minutes. For 5(6)-Carboxyfluorescein diacetate N-hydroxysuccinimidyl ester (CFSE, Abcam, Cambridge, Mass.) staining, CD38-control cells were prestained with 0.5 μmol/L CFSE for 15 minutes according to the manufacturer's specifications and mixed with unlabeled CD38+MM cells, followed by Cy3-labeled aptamer staining for 30 minutes. For antibody staining, cultured cells or mononuclear cells freshly isolated from MM patient bone marrow samples were stained with antibody (BioLegend) as specified for 15 minutes.

Immunoprecipitation and Western Blot Analysis

Immunoprecipitation with biotin-labeled aptamers was performed as previously reported (Shi, F., Cheng, Y. F., Wang, X. L., and Edge, A. S. 2010. Beta-catenin upregulates Atoh1 expression in neural progenitor cells by interaction with an Atoh1 3' enhancer. J Biol Chem 285:392-400). In brief, cells were lysed in radioimmunoprecipitation assay (RIPA) buffer supplemented with Halt protease and phosphatase inhibitor cocktail (Thermo Fisher Scientific). Biotin-labeled aptamers were incubated with lysates for 2 hours at 4° C. in SELEX binding buffer supplemented with Halt protease and phosphatase inhibitor cocktail. Aptamer-bound proteins were collected with streptavidin agarose resin (Thermo Fisher Scientific) following 1 hour incubation at 4° C. Precipitated proteins were washed 5 times with SELEX washing buffer supplemented with Halt protease and phosphatase inhibitor cocktail, boiled in sample buffer, and supernatants were analyzed by western blotting using an anti-CD38 antibody (Cell Signaling Technology, Danvers, Mass.). The biotin-labeled random library was used as a control and western blot was performed as previously reported (Wen, J., Feng, Y, Bjorklund, C. C., Wang, M., Orlowski, R. Z., Shi, Z. Z., Liao, B., O'Hare, J., Zu, Y, Schally, A. V., et al. 2011. Luteinizing Hormone-Releasing Hormone (LHRH)-I antagonist cetrorelix inhibits myeloma cell growth in vitro and in vivo. Mol Cancer Ther 10:148-158).

Determination of CD38-Specific Aptamer Biostability In Vitro and In Vivo

In vitro biostability of Aptamer#1S was evaluated as previously described (49). In brief, the aptamer was incubated with human serum (Atlanta Biologicals) for 24 hours, and samples were collected at different times using phenol-chloroform extraction. The amount of undigested aptamer was visualized on a 5% agarose gel. In vivo experiments were done in accordance with the institutional guidelines for the use of laboratory animals. To determine the in vivo biostability of Aptamer#1S, $2 \times 10^6$ RPMI8226GL and K299GL cells were inoculated subcutaneously into 8- to 10-week-old NOD/SCID IL2rg−/− mice (Jackson Laboratory, Bar Harbor, Me.). Tumor growth was monitored by weekly whole-body bioluminescence imaging using Xenogen IVIS imaging system (PerkinElmer, Waltham, Mass.). Once tumors formed, 5 ng Cy5.5-labeled APTAMER#1S dissolved in PBS was injected via the tail vein and its signal was monitored on the IVIS system.

DOX Loading into the CD38-Targeting Aptamer

DOX was purchased from Thermo Fisher Scientific. Since DOX preferentially binds to double-stranded 5'-GC-3' or 5'-CG-3' repeats (Meng, L., Yang, L., Zhao, X., Zhang, L., Zhu, H., Liu, C., and Tan, W. 2012. Targeted delivery of chemotherapy agents using a liver cancer-specific aptamer. PLoS One 7:e33434), CG repeats were added to the 5' end of Aptamer#1S to make the modified Aptamer#1S/CG-Cargo sequence. To determine the optimal molar ratio of aptamer to DOX, Apamer#1S/CG-Cargo sequence was heated at 95° C. for 5 minutes, cooled immediately on ice for 15 minutes, and then incubated with a fixed concentration of DOX (final concentration of DOX was 0.5 μmol/L) at various aptamer/DOX ratios ranging from 1:100 to 1:0.5. After 1 hour, the fluorescence ($\lambda_{Ex}$=488 nmol/L, $\lambda_{Em}$=590 nmol/L) was measured with a Synergy4 analyzer (BioTek, Winooski, Vt.). The minimal ratio at which the fluorescence of DOX was quenched to the maximal extent was determined as the optimal molar ratio (1:5 of aptamer to DOX) (29). To confirm that quenching of DOX fluorescence was exclusively caused by the intercalation of DOX into the aptamer/CG-Cargo sequence, 100 μL of the ApDC (final equivalent concentration of aptamer is 0.1 μmol/L and Dox is 0.5 μmol/L) was prepared in a 96-well dark plate and then digested with 2 units DNase I (Thermo Fisher Scientific), followed with fluorescence monitoring using Synergy4 analyzer.

Determination of ApDC Stability at Various Temperatures, pH Values, and in Human Serum ApDC was prepared such that its final equivalent concentration was 0.1 μmol/L (aptamer) and 0.5 μmol/L (DOX). To test ApDC stability at high temperatures, ApDC was heated from 25° C. to 95° C., and a melting curve was collected using a LightCycler (Roche Applied Science, Indianapolis, Ind.). To determine its stability in various pH solutions, 1 μL ApDC was mixed with 99 μL of binding buffer that was adjusted to pH values ranging from 7.4 to 1 (with hydrochloride acid) in a black 96-well plate, and fluorescence was monitored continuously. To evaluate ApDC stability under physiologic conditions, 1 μL of the ApDC was mixed with 99 μL human serum and fluorescence of the solution was monitored continuously.

Assessment of Selective ApDC Binding to and Uptake by CD38+ Cells

CD38+ MM and CD38− non-MM cells were incubated with free DOX (0.5 μmol/L final concentration) or ApDC (final equivalent concentration of aptamer was 0.1 μmol/L and DOX—0.5 μmol/L) for 1 hour. After washing, cells were resuspended with fresh medium, cultured for 2 hours, and then examined under a 40× objective (Olympus FV 1000 confocal microscope). DOX fluorescence was excited with a 5 mW, 488 nm Ar+ laser.

Assessment of ApDC Selective Apoptosis Induction

CD38+ MM cells and CD38− non-MM cells were treated with free DOX (1 μmol/L) or ApDC (final equivalent concentration of aptamer was 0.2 μmol/L and DOX—1 μmol/L) for 2 hour. After washing, cells were resuspended with fresh medium and cultured for 48 hours. Cells were then collected, stained with FITC-labeled annexin V (BD) and analyzed with flow cytometry. Alternatively, RPMI8226 and HDLM2 cell lines were lysed with RIPA buffer, and analyzed by western blotting using an anti-cleaved caspase 3 antibody (Cell Signaling).

Assessment of ApDC-Mediated Inhibition of Soft Agar Colony Formation

Soft agar colony formation assay was performed as previously reported. Briefly, 1.5 ml base agar layers of 0.6% agarose were prepared in 35 mm dishes by combining equal volumes of 1.2% low melting temperature agarose (Thermo Fisher Scientific) and 2×RPMI 1640+20% FBS+2× antibiotics. Then, $5 \times 10^3$ RPMI8226 or HDLM2 cells, pretreated with the free DOX (0.5 μmol/L) or ApDC (final equivalent concentration of aptamers was 0.1 μmol/L and DOX was 0.5 μmol/L) for 2 hour, were resuspended in 0.75 ml 2×RPMI 1640+20% FBS+2× antibiotics and mixed with 0.75 ml volumes of 0.6% agar, then immediately plated on top of base agar. PBS treatment was used as control. Cultures were overlaid with complete culture medium, which was changed twice a week. After 2 weeks, cultures were stained with methylene blue, pictures taken under a phase contrast microscope, and colony numbers counted.

Induction of Apoptosis in CD138+ Plasma Cells Isolated from Primary MM Bone Marrow Samples CD138+ and CD138− cells were isolated from primary MM bone marrow samples with CD138 antibody-conjugated magnetic beads (Miltenyi Biotec, Auburn, Calif.) as previously described (Wen, J., Feng, Y, Bjorklund, C. C., Wang, M., Orlowski, R. Z., Shi, Z. Z., Liao, B., O'Hare, J., Zu, Y, Schally, A. V., et al. 2011. Luteinizing Hormone-Releasing Hormone (LHRH)-I antagonist cetrorelix inhibits myeloma cell growth in vitro and in vivo. Mol Cancer Ther 10:148-158). Purity of CD138 separations was determined with PE-labeled CD38 antibody. Cells were then treated with free DOX (1 μmol/L) or ApDC (final equivalent concentration of aptamer was 0.2 μmol/L and DOX was 1 μmol/L) for 2 hours. After washing, cells were resuspended in fresh medium and cultured for 48 hours. Apoptosis rates were determined by staining cells with FITC-Annexin V and analyzing samples by flow cytometry.

Assessment of ApDC Tumor Inhibitory Effect in a MM Xenograft Mouse Model $0.5 \times 10^6$ RPMI8226 GL cells were inoculated bilaterally into tibiae of 8- to 10-week-old NOD/SCID IL2rg−/− mice.

Engraftment was monitored by weekly whole-body bioluminescence imaging on Xenogen IVIS imaging system, as previously reported (Wen, J., Feng, Y, Bjorklund, C. C., Wang, M., Orlowski, R. Z., Shi, Z. Z., Liao, B., O'Hare, J., Zu, Y, Schally, A. V., et al. 2011. Luteinizing Hormone-Releasing Hormone (LHRH)-I antagonist cetrorelix inhibits myeloma cell growth in vitro and in vivo. Mol Cancer Ther 10:148-158). Starting with day 6, mice were treated with free DOX (0.5 mg/kg) or an equivalent ApDC amount (6 mice per group) every other day (13 treatments total). Treatments were administered via the tail vein injection. Bioluminescence intensities representative of tumor mass were quantified by Living Image 3.1. Mice were euthanized by $CO_2$ as they became moribund and their survival curves were plotted with SPSS 10 statistical software (SPSS Inc., Chicago, Ill., USA). All experiments were approved by the IACUC of the Houston Methodist Research Institute. Cells isolated from tumor tissues were examined under a fluorescence microscope for GFP expression. Immunohistochemistry (IHC) against human CD38, human light chains Kappa and Lambda were performed as previously described (Wen, J., Feng, Y, Bjorklund, C. C., Wang, M., Orlowski, R. Z., Shi, Z. Z., Liao, B., O'Hare, J., Zu, Y, Schally, A. V., et al. 2011. Luteinizing Hormone-Releasing Hormone (LHRH)-I antagonist cetrorelix inhibits myeloma cell growth in vitro and in vivo. Mol Cancer Ther 10:148-158).

Measurement of inflammatory cytokines in ApDC-treated mice

To evaluate ApDC in vivo safety, BALB/c mice (6 mice per group, Charles River Laboratories, Portage, Mo.) were treated with the aptamer (4 mg/kg), free DOX (0.5 mg/kg), or ApDC (equivalent amount of aptamer is 4 mg/kg and DOX is 0.5 mg/kg) via the tail vein. Blood samples were collected after 3, 12, and 24 hours and levels of IFNγ, IL-1β, IL-2, IL-6, and TNFα were measured using Luminex-based murine multiplex assays (Millipore, St. Charles, Mo.) and with Luminex 200 system (Luminex, Austin, Tex.).

Statistical Analysis

Statistical analysis was conducted with SPSS 10 statistical software, using t-tests or one-way ANOVA.

What is claimed is:

1. A method of targeting CD38 cells with an agent, the method comprising conjugating a nucleic acid aptamer comprising a region that interacts with a CD38 cell to the agent, and exposing CD38 cells to the aptamer-agent conjugate, wherein the nucleic acid comprises SEQ ID NO: 1 or SEQ ID NO: 2.

2. The method of claim 1, wherein the nucleic acid aptamer comprises a G-C (guanine-cysteine) repeat region.

3. The method of claim 2, wherein the G-C repeat region is 5' or 3' of the region that interacts with CD38.

4. The method of claim 2, wherein the G-C repeat region comprises at least 80% guanine (G) and cysteine (C) nucleic acids.

5. The method of claim 2, wherein the aptamer comprises at least eight (8) consecutive guanine or cysteine nucleotides.

6. The method of claim 1, wherein the agent is a small molecule, organometallic compound, nucleic acid, protein, peptide, lipid, carbohydrate, hormone, metal, radioactive element, gelonin, phototoxic agent, drug, vaccine, or immunological agent.

7. The method of claim 1, wherein the agent is non-covalently associated with the nucleic acid and rapidly released from aptamer in a pH<5.5 environment.

8. The method of claim 2, wherein the agent intercalates in the G-C repeat region.

9. The method of claim 1, wherein the agent is a therapeutic agent.

10. The method of claim 9, wherein the therapeutic agent causes apoptosis of CD38-expressing cells.

* * * * *